US010154792B2

(12) United States Patent
Sakai et al.

(10) Patent No.: US 10,154,792 B2
(45) Date of Patent: Dec. 18, 2018

(54) STIMULATION DEVICE ADAPTER

(71) Applicants: Jonathan Sakai, Fairview Park, OH (US); Robert B. Strother, Willoughby Hills, OH (US); Joseph J. Mrva, Euclid, OH (US); Geoffrey B. Thrope, Shaker Heights, OH (US)

(72) Inventors: Jonathan Sakai, Fairview Park, OH (US); Robert B. Strother, Willoughby Hills, OH (US); Joseph J. Mrva, Euclid, OH (US); Geoffrey B. Thrope, Shaker Heights, OH (US)

(73) Assignee: CHECKPOINT SURGICAL, INC., Cleveland, OH (US)

( * ) Notice: Subject to any disclaimer, the term of this patent is extended or adjusted under 35 U.S.C. 154(b) by 343 days.

(21) Appl. No.: 14/019,170

(22) Filed: Sep. 5, 2013

(65) Prior Publication Data
US 2014/0073985 A1 Mar. 13, 2014

Related U.S. Application Data

(63) Continuation-in-part of application No. 13/934,384, filed on Jul. 3, 2013, which is a continuation of (Continued)

(51) Int. Cl.
*A61B 5/04* (2006.01)
*A61B 17/16* (2006.01)
(Continued)

(52) U.S. Cl.
CPC ........ *A61B 5/04001* (2013.01); *A61B 5/4887* (2013.01); *A61B 5/4893* (2013.01);
(Continued)

(58) Field of Classification Search
CPC ................... A61N 1/36014–1/36028
See application file for complete search history.

(56) References Cited

U.S. PATENT DOCUMENTS 4,072,154 A * 2/1978 Anderson ............ A61N 1/3752
174/152 GM
4,305,402 A 12/1981 Katims
(Continued)

FOREIGN PATENT DOCUMENTS

CN ZL20078006341.8 3/2012
CN 102553072 7/2012
(Continued)

OTHER PUBLICATIONS

International Search Report and the Written Opinion of the International Searching Authority, NDI Medical, LLC, PCT/US2007/01259, dated Jul. 21, 2008.
(Continued)

*Primary Examiner* — Jeffrey G Hoekstra
*Assistant Examiner* — Nicholas E Kolderman
(74) *Attorney, Agent, or Firm* — McDonald Hopkins LLC

(57) ABSTRACT

A stimulation device includes an adapter component to increase the usability of the stimulation device. The adapter may be a bipolar adapter arranged to connect to the housing of the stimulation device. The adapter may include a clip having a first channel configured to receive an operative element therein and a second channel having a return operative element therein. The return operative element is in electrical communication with an electrical circuit of said stimulation control device. Alternatively, the adapter may be a percutaneous adapter comprising a connector configured to connect to an operative element of a stimulation device and a lead wire connected to the connector. A needle may be connected to the lead wire to deliver a electrical stimulation (Continued)

signal to a target tissue located beneath the skin of a subject patient.

21 Claims, 23 Drawing Sheets

Related U.S. Application Data application No. 13/466,485, filed on May 8, 2012, now Pat. No. 8,500,652, which is a continuation of application No. 13/014,452, filed on Jan. 26, 2011, now Pat. No. 8,172,768, which is a continuation of application No. 11/651,165, filed on Jan. 9, 2007, now Pat. No. 7,878,981, which is a continuation-in-part of application No. 11/099,848, filed on Apr. 6, 2005, now Pat. No. 7,896,815, application No. 14/019,170, which is a continuation-in-part of application No. 11/337,319, filed on Jan. 23, 2006, now abandoned.

(60) Provisional application No. 60/657,277, filed on Mar. 1, 2005.

(51) Int. Cl.
  *A61B 17/88* (2006.01)
  *A61B 50/30* (2016.01)
  *A61B 5/00* (2006.01)
  *A61N 1/36* (2006.01)
  *A61B 17/00* (2006.01)
  *A61B 5/113* (2006.01)
  *A61B 90/00* (2016.01)

(52) U.S. Cl.
  CPC ...... *A61B 17/1626* (2013.01); *A61B 17/8875* (2013.01); *A61B 50/30* (2016.02); *A61B 5/1135* (2013.01); *A61B 5/4519* (2013.01); *A61B 90/04* (2016.02); *A61B 2017/00022* (2013.01); *A61B 2017/00154* (2013.01); *A61N 1/36014* (2013.01)

(56) References Cited

U.S. PATENT DOCUMENTS

| | | | |
|---|---|---|---|
| 4,515,168 A | 5/1985 | Chester et al. | |
| 4,545,374 A | 10/1985 | Jacobson | |
| 4,616,660 A | 10/1986 | Johns | |
| 4,632,121 A * | 12/1986 | Johnson | A61B 5/04286 439/346 |
| 4,777,960 A | 10/1988 | Berger et al. | |
| 4,817,628 A | 4/1989 | Zealear et al. | |
| 4,962,766 A | 10/1990 | Herzon | |
| 5,012,816 A | 5/1991 | Lederer | |
| 5,046,506 A | 9/1991 | Singer | |
| 5,086,788 A | 2/1992 | Castel et al. | |
| 5,251,637 A | 10/1993 | Shalvi | |
| 5,261,395 A * | 11/1993 | Oleen | A61N 1/3752 439/347 |
| 5,284,153 A | 2/1994 | Raymond et al. | |
| 5,284,154 A | 2/1994 | Raymond et al. | |
| 5,540,235 A | 7/1996 | Wilson | |
| 5,580,266 A * | 12/1996 | Shelly | H01R 13/53 439/281 |
| 5,775,331 A | 7/1998 | Raymond et al. | |
| 5,779,642 A | 7/1998 | Nightengale | |
| 5,797,835 A * | 8/1998 | Green | A61B 17/3401 600/106 |
| 5,879,289 A | 3/1999 | Yarush et al. | |
| 5,885,219 A | 3/1999 | Nightengale | |
| 5,928,158 A | 7/1999 | Aristides | |
| 6,091,995 A | 7/2000 | Ingle et al. | |
| 6,104,940 A * | 8/2000 | Watanabe | A61B 5/1486 600/345 |
| 6,139,545 A | 10/2000 | Utley et al. | |
| 6,167,291 A * | 12/2000 | Barajas | A61B 5/04286 439/909 |
| 6,292,701 B1 | 9/2001 | Prass et al. | |
| 6,304,785 B1 | 10/2001 | McCreery et al. | |
| 6,312,392 B1 | 11/2001 | Herzon | |
| 6,325,764 B1 | 12/2001 | Griffith et al. | |
| 6,334,068 B1 | 12/2001 | Hacker | |
| 6,356,783 B1 * | 3/2002 | Hubbard, Jr. | A61B 5/0492 600/546 |
| 6,473,511 B1 | 10/2002 | Aceti et al. | |
| 6,494,882 B1 | 12/2002 | Lebouitz et al. | |
| 6,535,759 B1 * | 3/2003 | Epstein | A61N 1/36014 600/547 |
| 6,542,260 B1 | 4/2003 | Gann et al. | |
| 6,609,018 B2 | 8/2003 | Cory et al. | |
| 6,612,983 B1 | 9/2003 | Marchal | |
| 6,618,626 B2 | 9/2003 | West, Jr. et al. | |
| 6,654,634 B1 | 11/2003 | Prass | |
| 6,829,508 B2 | 12/2004 | Schulman et al. | |
| 6,972,199 B2 | 12/2005 | Lebouitz et al. | |
| 6,975,708 B1 | 12/2005 | Scherer | |
| 7,010,352 B2 | 3/2006 | Hogan | |
| 7,142,917 B2 | 11/2006 | Fukui | |
| 7,174,218 B1 | 2/2007 | Kuzma | |
| 7,207,949 B2 | 4/2007 | Miles et al. | |
| 7,282,033 B2 | 10/2007 | Urmey | |
| 7,359,751 B1 * | 4/2008 | Erickson | A61N 1/37241 607/27 |
| 7,470,236 B1 | 12/2008 | Kelleher et al. | |
| 7,522,953 B2 | 4/2009 | Kaula et al. | |
| 7,555,347 B2 | 6/2009 | Loeb | |
| 7,678,107 B2 | 3/2010 | Young | |
| 7,775,824 B2 * | 8/2010 | Weigand | H01R 13/506 439/357 |
| 7,878,981 B2 * | 2/2011 | Strother | A61B 17/1626 600/554 |
| 7,896,815 B2 | 3/2011 | Thrope et al. | |
| 8,172,768 B2 | 5/2012 | Strother et al. | |
| 8,273,084 B2 * | 9/2012 | Kunis | A61B 18/1492 606/41 |
| 8,500,652 B2 | 8/2013 | Strother et al. | |
| 8,515,555 B1 * | 8/2013 | Jones | A61N 1/3752 607/115 |
| 2002/0120259 A1 | 8/2002 | Lettice et al. | |
| 2003/0004549 A1 | 1/2003 | Hill et al. | |
| 2004/0078056 A1 | 4/2004 | Zangen et al. | |
| 2004/0215184 A1 | 10/2004 | Eggers et al. | |
| 2005/0075701 A1 | 4/2005 | Shafer | |
| 2005/0113818 A1 * | 5/2005 | Sartor | A61B 18/1206 606/34 |
| 2005/0118887 A1 * | 6/2005 | Hoffer | H01R 13/5224 439/810 |
| 2005/0131402 A1 * | 6/2005 | Ciarrocca | A61B 18/1402 606/41 |
| 2005/0171576 A1 * | 8/2005 | Williams | A61N 1/36017 607/48 |
| 2005/0187512 A1 | 8/2005 | Isola et al. | |
| 2005/0197675 A1 | 9/2005 | David et al. | |
| 2005/0256523 A1 * | 11/2005 | Chen | A61B 18/14 606/41 |
| 2005/0256541 A1 | 11/2005 | Stypulkowski | |
| 2006/0011022 A1 | 1/2006 | Fairburn et al. | |
| 2006/0025702 A1 * | 2/2006 | Sterrantino | A61B 5/0488 600/554 |
| 2006/0058854 A1 * | 3/2006 | Abrams | A61N 1/36021 607/45 |
| 2006/0200219 A1 | 9/2006 | Thrope et al. | |
| 2007/0032789 A1 * | 2/2007 | Gonnering | A61B 18/14 606/42 |
| 2007/0149011 A1 * | 6/2007 | Kent | H01R 13/508 439/120 |
| 2007/0178717 A1 * | 8/2007 | Harshman | H01R 13/5224 439/53 |
| 2008/0039915 A1 * | 2/2008 | Van Den Biggelaar | A61N 1/0492 607/116 |

(56) References Cited

U.S. PATENT DOCUMENTS

| | | | |
|---|---|---|---|
| 2008/0234767 A1* | 9/2008 | Salmon | A61N 1/37247 607/2 |
| 2008/0300491 A1* | 12/2008 | Bonde | A61B 17/3403 600/461 |
| 2009/0054890 A1 | 2/2009 | DeCarlo | |
| 2009/0157091 A1* | 6/2009 | Buysman | A61N 1/0551 606/129 |
| 2009/0299417 A1* | 12/2009 | Schoenbach | A61N 1/327 607/2 |
| 2010/0136856 A1* | 6/2010 | Gleason | A61B 18/14 439/886 |
| 2011/0045680 A1* | 2/2011 | Beller | A61B 18/14 439/188 |
| 2011/0060242 A1 | 3/2011 | Hausman et al. | |
| 2011/0288451 A1* | 11/2011 | Sanai | A61B 17/320092 601/2 |
| 2012/0265196 A1* | 10/2012 | Turner | A61B 17/320092 606/34 |
| 2013/0289439 A1 | 10/2013 | Hacker et al. | |

FOREIGN PATENT DOCUMENTS

| | | |
|---|---|---|
| CN | 104321012 | 1/2015 |
| DE | 37 19 353 | 12/1988 |
| DE | 100 54 405 | 5/2002 |
| JP | 09-504704 | 5/1997 |
| JP | 09-215757 | 8/1997 |
| JP | 2002-528039 | 8/2002 |
| JP | 2003-503119 | 1/2003 |
| JP | 2004-500917 | 1/2004 |
| JP | 2004-508875 | 3/2004 |
| JP | 2004-275427 | 7/2004 |
| JP | 2005-525861 | 9/2005 |
| WO | WO94/00191 | 1/1994 |
| WO | WO97/045156 | 12/1997 |
| WO | WO01/00273 | 1/2001 |
| WO | WO01/52932 | 7/2001 |
| WO | WO01/80755 | 11/2001 |
| WO | WO02/24089 | 3/2002 |
| WO | WO03/005887 | 1/2003 |
| WO | WO 03/033068 A2 * | 4/2003 |
| WO | WO03/096880 | 11/2003 |
| WO | WO2004/075974 | 9/2004 |
| WO | WO2005112813 | 12/2005 |
| WO | WO2007/117344 | 10/2007 |

OTHER PUBLICATIONS

International Preliminary Examination Report, NDI Medical, LLC, PCT/US2007/01259, dated Oct. 31, 2008.

Mittal, Suneet, M.D., et al., The Atrioventricular Nodal Fat Pad in Humans: Fat or Fiction?, Journal of Cardiovascular Electrophysiology, pp. 740-741, vol. 13, No., Aug. 2002.

European Supplementary Search Report, NDI Medical, LLC, Application No. 0776987.1-1265, dated Jan. 21, 2010.

International Search Report and the Written Opinion of the International Searching Authority, Checkpoint Surgical, LLC, PCT/US2013/058270, dated Mar. 19, 2014.

Tsuboi, Masato et al., Inotropic, Chronotropic, and dromotropic effects medicated via parasympathetic ganglia in the dog heart, Am. J. Physiol Heart Cir. Physiol 279, pp. H1201-H1207, vol. 279, 2000.

Verrier, Richard L. et al., Autonomic aspects of arrhythmogenesis: the enduring and the new, Lippincott Williams & Wilkins, 19:2-11, 2004.

Markowitz, Steven et al., Time Course and Predictors of Autonomic Dysfunction After Ablation of the Slow Atrioventricular Nodal Pathway, PACE, pp. 1638-1643, vol. 27, Dec. 2004.

Patent Abstracts of Japan, Device for Medical use for Processing Upper Airway Fault, Publication JP 09-21575, Medtronic Inc., Aug. 19, 1997.

Translation of Publication JP 2004-508875, Fluid-Assisted Medical Device, Tissuelink Medical, Inc., Mar. 25, 2004.

Translation of Publication JP 2004-500917, Suction Stabilized Epicardial Ablation Devices, Medtronic, Inc., Jan. 15, 2004.

Translation of Publication JP 2003-503119, Devices and Methods for Vagus Nerve Stimulation, Emory University, Jan. 28, 2003.

Translation of Publication JP 2002-528039, Tissue Heating and Ablation Systems and Methods Using Porous Electrode Structures, EP Technologies, Inc., Aug. 27, 2002.

Translation of Publication JP 09-504704, Method and Apparatus for Discrimination of Ventricular and Supraventricular Tachycardia and Method and Apparatus for Discriminating Between a Rapid Heart Rhythm of Sinus Origin and Rapid Heart Rhythm of Non-Sinus Origin, Medtronic, Inc., May 13, 1997.

Translation of Publication JP 2004-275427, Heart Treatment Equipment, Terumo Corp., Jul. 10, 2004.

Translation of Publication JP 2005-525861, Fluid-Assisted Medical Devices, Systems and Methods, Tissuelink Medical, Inc., Sep. 2, 2005.

Cummings, Jennifer E. et al., Preservation of the Anterior Fat Pad Paradoxically Decreases the Incidence of Postoperative Atrial Fibrillation in Humans, Journal of the American College of Cardiology, pp. 995-1000, vol. 43, No. 6, Mar. 17, 2004.

http://www.bioenteprise.com/companies/index.html, p. 2, Nov. 9, 2005.

http://www.hrsonline.org/professional_education/learning_categories/articles/mazgalev_5 . . . , Heart Rhythm Society, p. 1, Nov. 29, 2005.

http://www.ebcid:com.britannica.oec2.identifier.ArticleIdentifier?tocID=90322, Article: electrocardiography, 2 pages, Nov. 29, 2005.

http://www.ebcid:com.britannica.oec2.identifier.AssemblyIdentifier?assemblyl . . . , Article: electrocardiography: normal electrocardiogram and heart, 1 page, Nov. 29, 2005.

http://www.ebcid:com.britannica.oec2.identifier.ArticleIdentifier?tocID=33620& . . . , Article: cardiovascular disease, pp. 1-70, Nov. 29, 2005.

Nakajima, Koichi et al., Autonomic Control of the Location and Rate of the Cardiac Pacemaker in the Sinoatrial Fat Pad of Parasympathetically Denervated Dog Hearts, Journal of Cardiovascular Electrophysiology, vol. 13, No. 9, Sep. 2002.

Carlson, Mark D. et al., Selective Stimulation of Parasympathetic Nerve Fibers to the Human Sinoatrial Node, American Heart Association, 1992; 85:1311-1317.

Quan, Kara J. et al., Identification and Characterization of Artioventricular Parasympathetic Innervation in Humans, Journal of Cardiovascular Electrophysiology, pp. 735-739, vol. 13, No. 8, Aug. 2002.

* cited by examiner

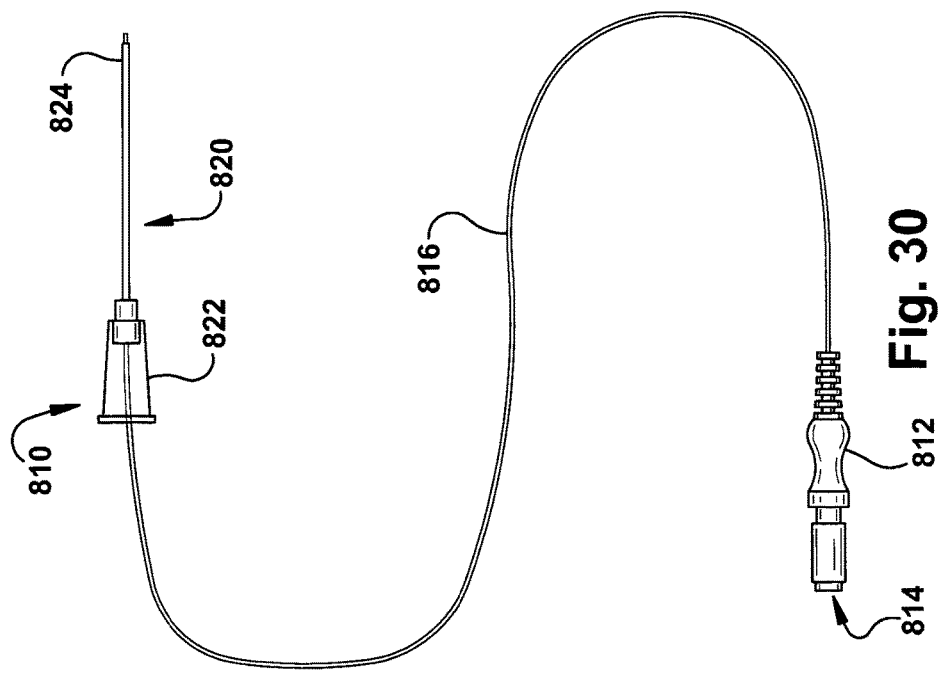
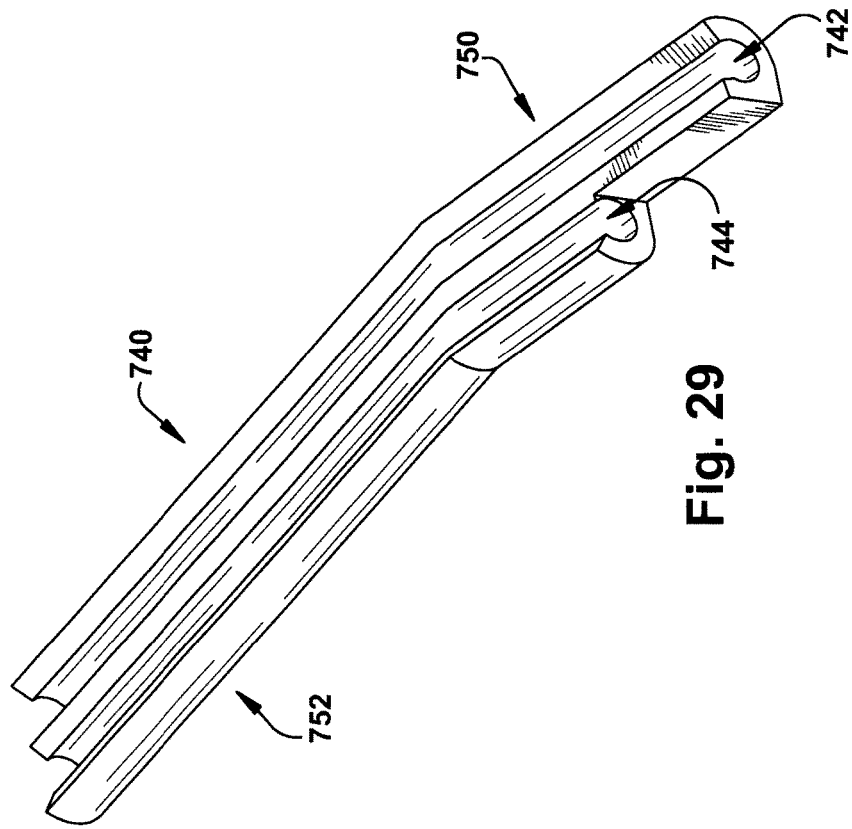

STIMULATION DEVICE ADAPTER

RELATED APPLICATIONS

This application is a continuation-in-part of co-pending U.S. patent application Ser. No. 13/934,384 filed on Jul. 3, 2013 and entitled "Systems and Methods for Intra-Operative Stimulation,", which is a continuation of co-pending U.S. patent application Ser. No. 13/466,485, filed Sep. 20, 2012, and entitled "Systems and Methods for Intra-Operative Stimulation," which is a continuation of co-pending U.S. patent application Ser. No. 13/014,452, filed Jan. 26, 2011, and entitled "Systems and Methods for Intra-Operative Stimulation," which is a continuation of co-pending U.S. patent application Ser. No. 11/651,165, filed Jan. 9, 2007, and entitled "Systems and Methods for Intra-Operative Stimulation," which is a continuation-in-part of U.S. patent application Ser. No. 11/099,848, filed Apr. 6, 2005, and entitled "Systems and Methods for Intra-Operative Stimulation," which claims the benefit of U.S. Provisional Patent Application Ser. No. 60/657,277, filed Mar. 1, 2005, and entitled "Systems and Methods for Intra-Operative Stimulation," and also a continuation-in-part of co-pending U.S. patent application Ser. No. 11/337,319 filed on Jan. 23, 2006 and entitled "Systems and Methods for differentiating and/or identifying tissue regions innervated by targeted nerves for diagnostic and/or therapeutic purposes," all of which are incorporated herein by reference in their entireties.

FIELD OF THE INVENTION

The invention relates generally to tissue identification and integrity testing, and more particularly to systems and methods for safeguarding against nerve and muscle injury during surgical procedures, location and stimulation of nerves and muscles, identification and assessment of nerve and muscle integrity following traumatic injuries, and verification of range of motion and attributes of muscle contraction during reconstructive surgery.

BACKGROUND OF THE INVENTION

Even with today's sophisticated medical devices, surgical procedures are not risk-free. Each patient's anatomy differs, requiring the surgeon to be ever vigilant to these differences so that the intended result is accomplished. The positioning of nerves and other tissues within a human or animal's body is one example of how internal anatomy differs from patient to patient. While these differences may be slight, if the surgeon fails to properly identify one or several nerves, the nerves may be bruised, stretched, or even severed during an operation. The negative effects of nerve damage can range from lack of feeling on that part of the body to loss of muscle control.

Traumatic injuries often require surgical repair. Determining the extent of muscle and nerve injury is not always possible using visual inspection. Use of an intra-operative stimulator enables accurate evaluation of the neuromuscular system in that area. This evaluation provides valuable knowledge to guide repair/reconstructive surgery following traumatic injury, and when performing a wide range of surgeries.

It may be desirable for diagnostic and/or therapeutic reasons to differentiate and/or identify within a tissue region the presence of targeted sympathetic nerves and/or parasympathetic nerves. Further, it may be desirable to target specific nerves and tissue regions and limit stimulation to the targeted areas.

SUMMARY OF THE INVENTION

The invention provides devices, systems, and methods for intra-operative stimulation that enable accurate evaluation of the neuromuscular system to guide repair or reconstructive surgery.

One aspect of the invention provides devices, systems, and methods comprising a tissue stimulation system having a housing having a proximal end and a distal end, an operative element having an electrically conductive surface sized and configured for electrical stimulation of a targeted tissue region, and the operative element extends from the proximal end of the housing. The housing proximal end may comprise an operative element adjustment portion to allow movement of the operative element, with the electrical stimulation being in the form of a stimulation signal having an amplitude and a duration for providing a first indication. A stimulation control device is electrically coupled to the operative element, the stimulation control device comprising a power source and stimulation signal generating circuitry. The tissue stimulation system may conform to the IPX1 water ingress standard.

In one aspect of the invention, the stimulation control device is positioned within the housing. The housing may comprise a gripping base portion and the operative element adjustment portion. The operative element adjustment portion comprises a flexible nose cone.

The first indication comprises a visual indication located on the housing, and the housing may be tubular. The visual indication may also include a reflective element. The visual indication may comprise an illuminating circumferential ring indicator, the illuminating circumferential ring indicator being visible around the circumference of the tubular housing.

Yet another aspect of the invention provides devices, systems, and methods comprising a tissue stimulation system comprising a housing, such as a tubular shaped housing, having a proximal end and a distal end, an operative element having an electrically conductive surface sized and configured for electrical stimulation of a targeted tissue region, the operative element extending from the proximal end of the housing, and wherein the electrical stimulation is in the form of a signal having an amplitude and a duration for providing a first indication to the user of close proximity of the operative element to the targeted tissue region, and a stimulation control device electrically coupled to the operative element, the stimulation control device comprising stimulation signal generating circuitry. The housing may include a first control device for turning the stimulation signal to the operative element on and off and for providing adjustment of the stimulation signal amplitude, the first control device being electrically coupled to the stimulation control device. The housing may also include a second control device for providing adjustment of the stimulation signal duration, the second control device being electrically coupled to the stimulation control device.

Additional aspects of the invention provide a tissue stimulation system that may be sterilized using ethylene oxide, for example, and prepackaged for single use. The stimulation signal of the tissue stimulation system includes an amplitude that may range between about zero milliamps and about 20 milliamps, allowing for accurate selective stimulation of both muscles and nerves, and also identification of nerves and muscles, muscle attachments, or to contract muscles to assess the quality of surgical interventions. The tissue stimulation signal duration may include a range between about zero microseconds and about 200 microseconds, for example. The first indication provided by the tissue stimulation system may include, for example, audio and visual indications. The tissue stimulation system may further include a second indication means to provide confirmation of power on to the device and delivery of a stimulation signal to the electrically conductive surface. The first and second indication means may be combined into a single indication means. The operative element of the tissue stimulation system may comprise a probe, for example, where the electrically conductive surface of the probe comprises between about 1 millimeter and about 10 millimeters of the proximal end of the probe, and the probe comprises a diameter between about 0.5 millimeters and about 1.5 millimeters. The tissue stimulation system may also further include a return electrode electrically coupled to the stimulation control device.

Additional aspects of the invention provide a tissue stimulation system, such as a medical device comprising a housing having a proximal end and a distal end, the housing sized and configured to be held by a user in either the left or right hand, a probe having an electrically conductive surface sized and configured for electrical stimulation of a targeted tissue region, the probe extending from the proximal end of the housing. The housing proximal end may comprise a probe adjustment portion to allow movement of the probe. The electrical stimulation is in the form of a signal having an amplitude and a duration for providing a physical motor response, a stimulation control device electrically coupled to the probe and sized and configured to be positioned within the housing, the stimulation control device comprising stimulation signal generating circuitry. The housing may include a first control device for turning the stimulation signal to the probe on and off and for providing adjustment of the stimulation signal amplitude, the first control device being electrically coupled to the stimulation control device. The housing may also include a second control device for providing adjustment of the stimulation signal duration, the second control device being electrically coupled to the stimulation control device.

According to another aspect of the invention, a stimulation control device electrically coupled to at least one surgical tool, which can comprise, e.g., a cutting, grasping, drilling, screwing, and/or viewing tool. The application of stimulation voltage or current to the device allows the clinician to observe muscle contraction or changes in the nervous system response when the surgical tool is in close proximity to viable nerve or muscle tissue. The surgical tool thus becomes a neural/muscular stimulating electrode. In use, different surgical tools, individually deployed in association with different medical procedures, can make use of a singe, stimulation control device, to which a selected surgical tool can be temporarily coupled for use.

According to yet another aspect of the invention, the stimulation control device may be embedded within the surgical tool to provide a medical device capable of providing stimulation, as described above.

Another aspect of the invention provides devices, systems, and methods comprising a stimulation monitor or probe and at least one electrode. In one embodiment, a hand held stimulation probe or monitor includes the stimulation control device and at least one stimulation electrode within a unified housing to provide an ergonomic stimulation device. The hand held stimulation probe can be a sterile, single use instrument intended for use during surgical procedures to identify nerves and muscles, muscle attachments, or to contract muscles to assess the quality of surgical interventions or the need for surgical interventions, or to evaluate the function of nerves already identified through visual or audible means, or by other nervous system monitoring instruments.

Yet another aspect of the invention provides devices, systems, and methods, including a method of testing a tissue region of a patient that includes providing a tissue stimulation system having an operative element extending from a proximal end of a housing, the housing proximal end may comprise an operative element adjustment portion to allow movement of the operative element, moving a first control device to an activation position causing a stimulation signal to be generated by the stimulation system and transmitted to the operative element, engaging the patient with the operative element at a targeted tissue region, and observing the targeted tissue region for a first indication.

The method may further include engaging the patient with a second electrode which is electrically coupled to the stimulation system, the second electrode allowing the stimulation signal to flow from the operative element, through the patient's body to the second electrode, and back to the stimulation system.

Another aspect of the invention provides devices, systems, and methods comprising a hand held tissue stimulation apparatus including a tubular shaped housing comprising a gripping base portion and an operative element adjustment portion, the gripping base portion comprising a first housing element and a second housing element, a stimulation control device positioned within the gripping base portion, a battery positioned within the gripping base portion and coupled to the stimulation control device to provide power to the stimulation control device, a visual indication coupled to a proximal end of the gripping base portion, the visual indication comprising an illuminating circumferential ring indicator, the illuminating circumferential ring indicator being visible around the circumference of the tubular housing, and an operative element having an electrically conductive surface sized and configured for electrical stimulation of a targeted tissue region, the operative element being coupled to the stimulation control device and extending from the proximal end of the operative element adjustment portion.

The operative element adjustment portion may comprise a flexible nose cone sized and configured to allow movement of the operative element, and the visual indication further includes a reflector element. A return electrode electrically may be coupled to the stimulation control device.

According to yet another aspect of the invention, a kit of devices provides tissue stimulation to a targeted tissue region. The kit may include a hand held stimulation probe including a housing sized and configured to be held with either a left or right hand, the stimulation probe being sterilized and disposable, and including an operative element extending from a proximal end of the housing, the housing proximal end may comprise an operative element adjustment portion to allow movement of the operative element, a lead including a return electrode coupled to the stimulation probe, and instructions for use describing the unpacking and tissue contact procedure for the stimulation probe.

Additional aspects of the invention provide a stimulation control device electrically coupled to a tissue cutting instrument, or a stimulation control device electrically coupled to a drilling instrument, or a stimulation control device electrically coupled to a pilot auger for hard surface rotary probing prior to pilot hole drilling, or a stimulation control device electrically coupled to a fixation device, which is commonly used in spinal stabilization procedures and internal bone fixation procedures.

In another aspect, the invention provides a first device for generating and applying a stimulation current to tissue. The devices, systems, and methods also include a second device for sensing the presence or absence of an anticipated physiologic response to the application of the electrical stimulation current. The presence of the anticipated physiologic response indicates the innervation of targeted nerve fibers or branches within the tissue region. Once differentiated and identified, the targeted nerve fibers or branches can be manipulated to achieve desired diagnostic and/or therapeutic outcomes.

The devices, systems, and methods are well suited, e.g., for differentiating and/or identifying localized branches of the vagus nerve. The vagus nerve runs from the brain through the face and thorax to the abdomen. It is a mixed nerve that contains parasympathetic fibers. The vagus nerve has the most extensive distribution of the cranial nerves. Its pharyngeal and laryngeal branches transmit motor impulses to the pharynx and larynx; its cardiac branches act to slow the rate of heartbeat; its bronchial branch acts to constrict the bronchi; and its esophageal branches control involuntary muscles in the esophagus, stomach, gallbladder, pancreas, and small intestine, stimulating peristalsis and gastrointestinal secretions. Being able to differentiate and/or identify the presence of a branch of the vagus nerve within a given tissue region within the body makes possible the development and application of diverse diagnostic and/or therapeutic techniques for parasympathetic mediation of a diverse number of anatomic functions, e.g., in the digestive system, the respiratory system, or the heart.

For example, one aspect of the invention provides devices, systems, and methods that make possible the differentiation and identification of the epicardial fat pads on the surface of the heart, which are innervated by parasympathetic vagal nerve fibers. The devices, systems, and methods thereby make it possible to access the parasympathetic nervous system of the heart for therapeutic benefits, such as to control the ventricular rate or to provide physiologic control of the AV nodal rate.

Another aspect of the invention provides systems and methods for treating a heart comprising locating a fat pad region on a heart innervated by parasympathetic nerves using a first device for generating and applying a stimulation current, and then manipulating the parasympathetic nervous system of the heart in the region of the fat pad for diagnostic or therapeutic benefit.

In an embodiment, the an adapter is provided. The adapter may be configured to connect to the stimulation control device. The adapter may be a bipolar adapter arranged to connect to the housing of the stimulation device. The adapter may include a clip having a first channel configured to receive an operative element therein and a second channel having a return operative element therein. The return operative element is in electrical communication with an electrical circuit of said stimulation control device.

In an embodiment, the adapter may be a percutaneous adapter comprising a connector configured to connect to an operative element of a stimulation device and a lead wire connected to the connector. A needle may be connected to the lead wire to deliver a electrical stimulation signal to a target tissue located beneath the skin of a subject patient.

Features and advantages of the inventions are set forth in the following Description and Drawings, as well as the appended description of technical features.

BRIEF DESCRIPTION OF THE DRAWINGS

FIG. 29 is unitary clip.

FIG. 30 is a percutaneous adapter.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF PREFERRED EMBODIMENTS

This Specification discloses various systems and methods for safeguarding against nerve, muscle, and tendon injury during surgical procedures or confirming the identity and/or location of nerves, muscles, and tendons and evaluating their function or the function of muscles enervated by those nerves. The systems and methods are particularly well suited for assisting surgeons in identification of nerves and muscles in order to assure nerve and muscle integrity during medical procedures using medical devices such as stimulation monitors, cutting, drilling, and screwing devices, pilot augers, and fixation devices. For this reason, the systems and methods will be described in the context of these medical devices.

The systems and methods desirably allow the application of a stimulation signal at sufficiently high levels for the purposes of locating, stimulating, and evaluating nerve or muscle, or both nerve and muscle integrity in numerous medical procedures, including, but not limited to, evaluating proximity to a targeted tissue region, evaluating proximity to a nerve or to identify nerve tissue, evaluating if a nerve is intact (i.e., following a traumatic injury) to determine if a repair may be needed, evaluating muscle contraction to determine whether or not the muscle is innervated and/or whether the muscle is intact and/or whether the muscle is severed, and evaluating muscle and tendon length and function following a repair or tendon transfer prior to completing a surgical procedure.

Still, it should be appreciated that the disclosed systems and methods are applicable for use in a wide variety of medical procedures with a wide variety of medical devices. By way of non-limiting example, the various aspects of the invention have application in procedures requiring grasping medical devices and internal viewing devices as well.

I. Overview of the System

Figure 1:
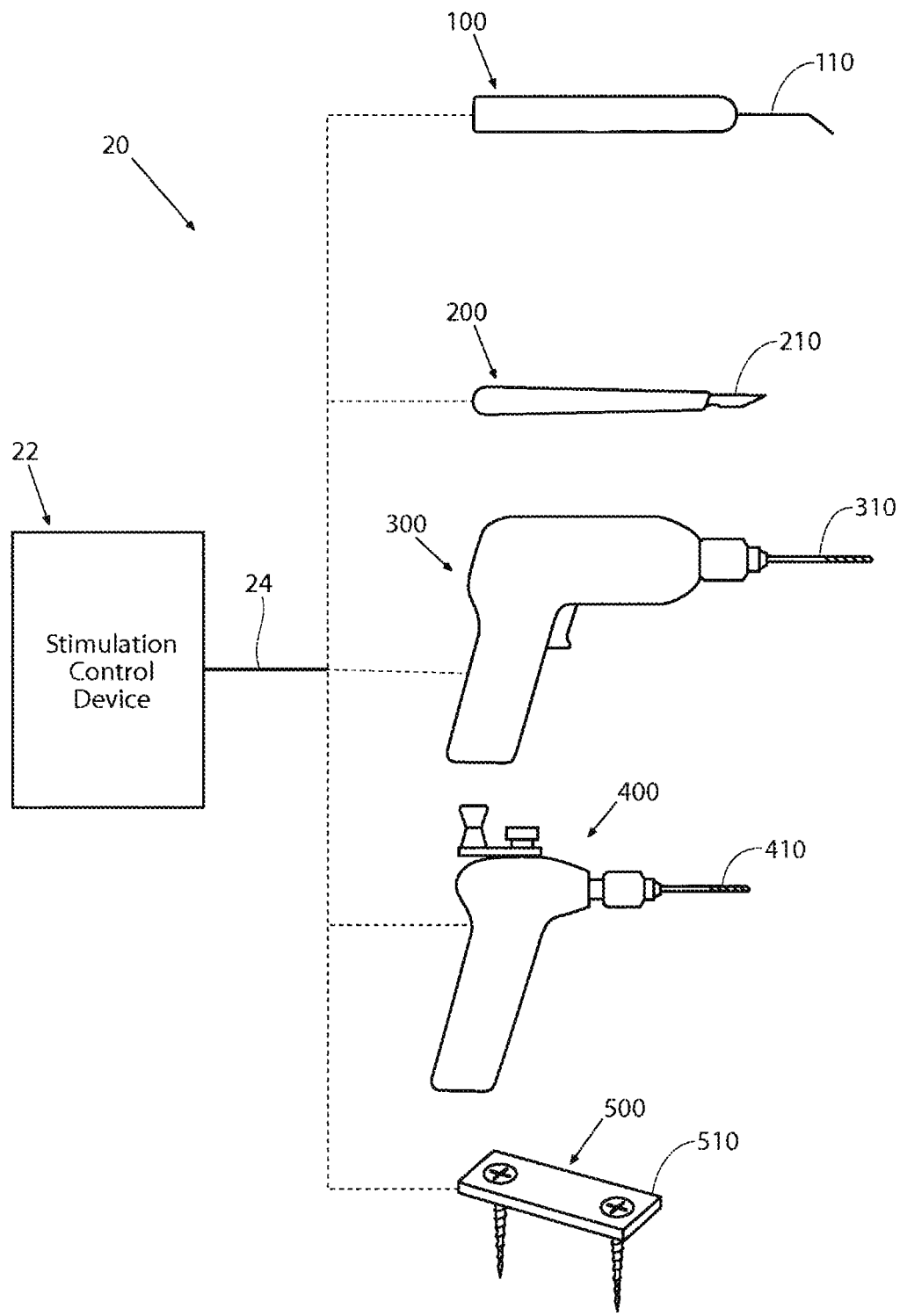
FIG. 1 is a diagrammatic view of a system usable in association with a family of different monitoring and treatment devices for use in different medical procedures.

FIG. 1 shows an illustrative system 20 for locating and identifying tissue and safeguarding against tissue and/or bone injury during surgical procedures. In the illustrated embodiment, the system 20 is configured for locating, monitoring, and stimulating tissue and other structures throughout the body. The system 20 includes a stimulation control device 22 operating individually or in conjunction with one or more of a family of stimulating medical devices including, for example, a stimulation monitor or probe 100, a cutting device 200, a drilling or screwing device 300, a pilot auger 400, and a fixation device 500.

Figure 2:
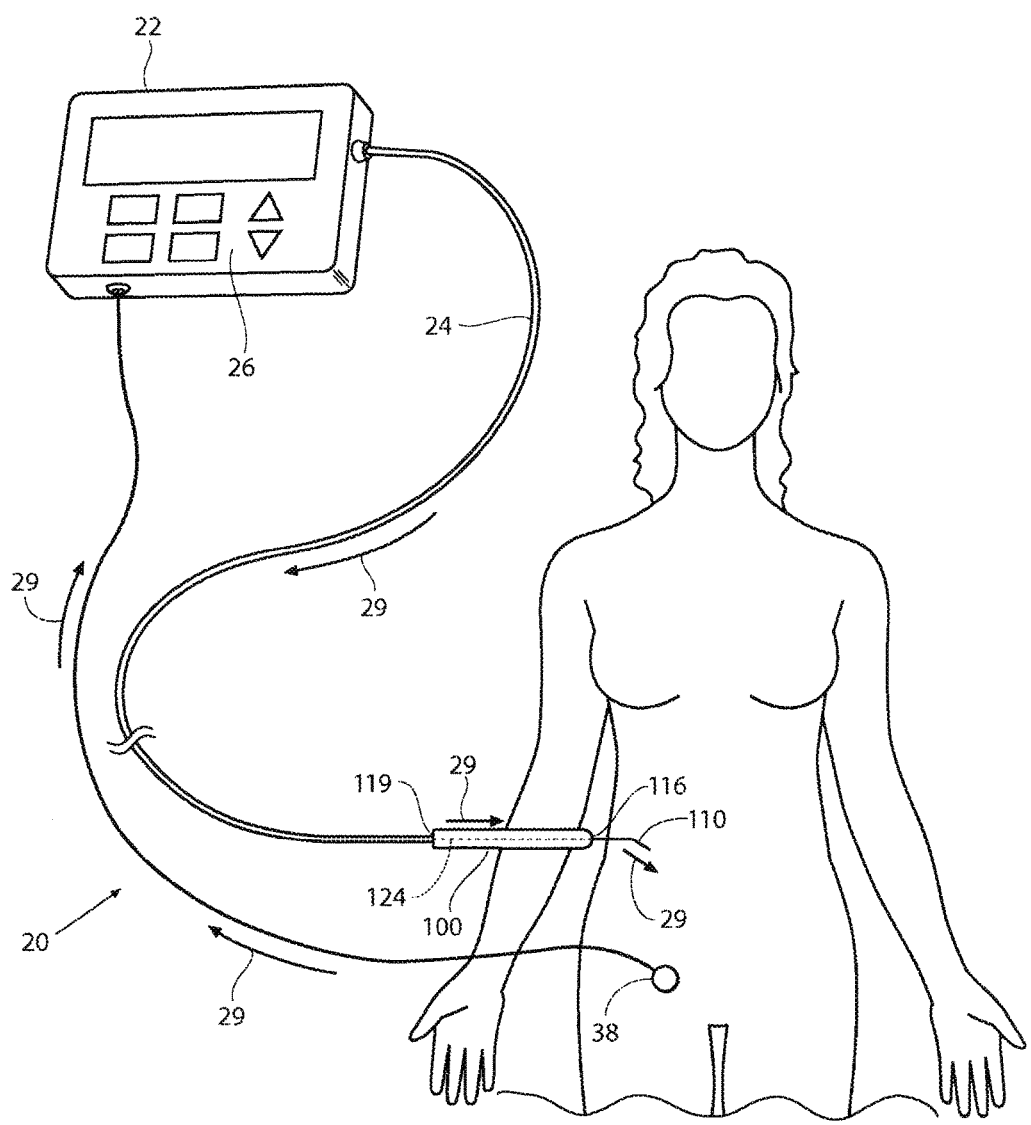
FIG. 2 is a perspective view showing an exemplary embodiment of the system shown in FIG. 1, the stimulation control device being removably coupled to a stimulation probe, and showing the stimulation signal path through the system.

In an exemplary embodiment, and as can be seen in FIG. 2, the stimulation control device 22 functions in the system 20 to generate an electrical stimulation signal 29. The stimulation signal 29 flows from the stimulation control device 22 through a lead 24 to a medical device (e.g., stimulation probe 100). The stimulation signal 29 then flows through a predefined insulated path 124 within the stimulation probe 100 and to an operative element, such as an electrically conductive surface, i.e., a coupled electrode 110. The electrode 110 is to be positioned on or near a region of a patient to be stimulated. In monopolar operation, a return electrode (or indifferent electrode) 38 provides an electrical path from the body back to the control device 22. The stimulation control device 22 may operate in a monopolar or bipolar configuration, as will be described in greater detail later.

The stimulation signal 29 is adapted to provide an indication or status of the device. The indication may include a physical motor response (e.g., twitching), and/or one or more visual or audio signals from the stimulation control device 22, which indicate to the surgeon the status of the device, and/or close proximity of the electrode 110 to a nerve, or a muscle, or a nerve and a muscle. The stimulation control device may also indicate to the surgeon that the stimulation control device is operating properly and delivering a stimulus current.

II. Medical Devices

The configuration of the stimulating medical devices that form a part of the system can vary in form and function. Various representative embodiments of illustrative medical devices will be described.

A. Stimulation Probe

Figure 3A:
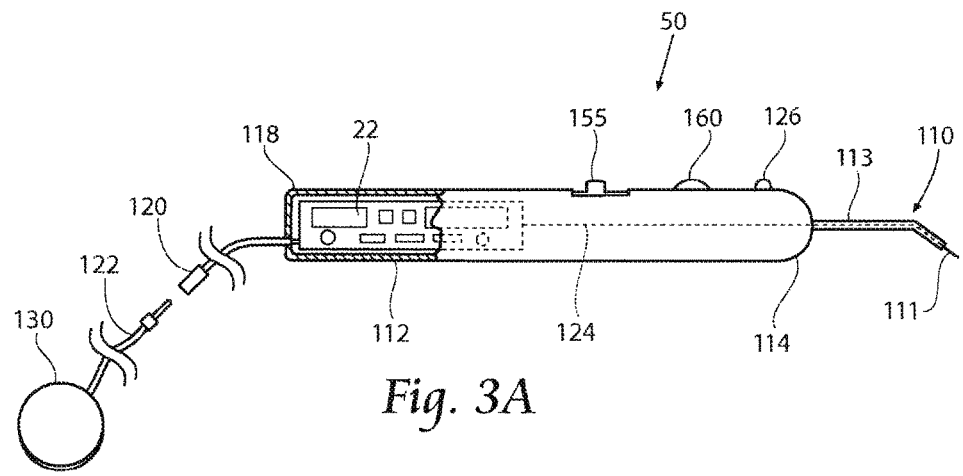
FIG. 3A is a side view with a portion broken away and in section showing the stimulation probe having the stimulation control device embedded within the stimulation probe.
Figure 3B:
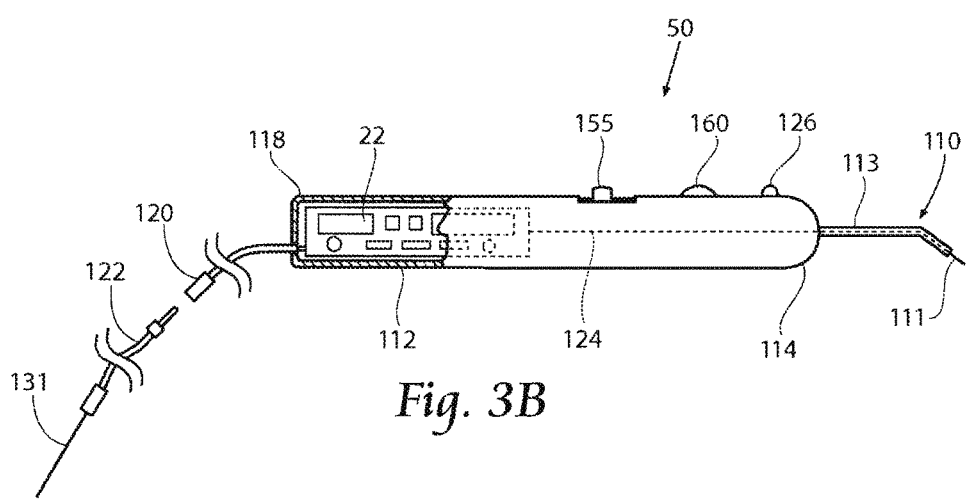
FIG. 3B is a side view with a portion broken away and in section showing the stimulation probe having the stimulation control device embedded within the stimulation probe, and showing an optional needle-like return electrode.
Figure 3C:
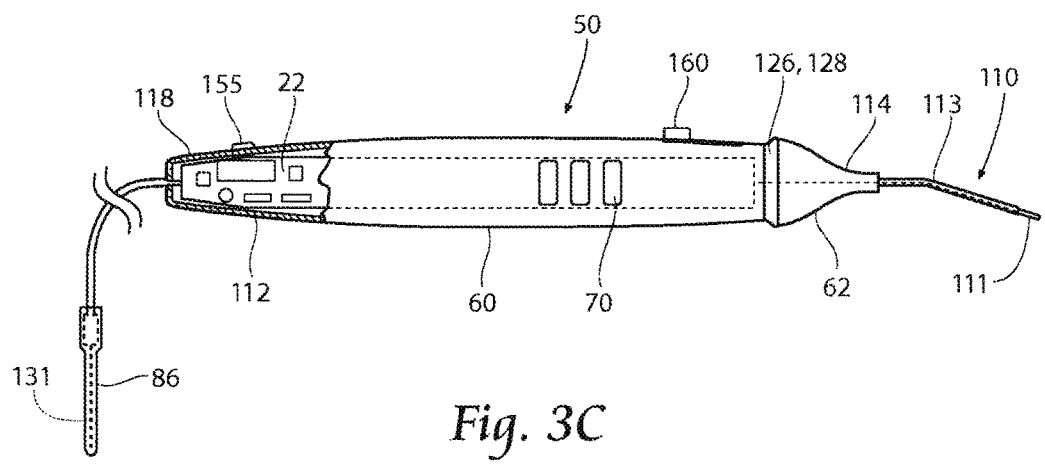
FIG. 3C is a side view with a portion broken away and in section showing an additional embodiment of the stimulation probe having a housing that includes a gripping base and a flexible nose cone, and an illuminating ring indicator.

FIGS. 3A to 3C show various embodiments of a hand held stimulation monitor or probe 50 for identification and testing of nerves and/or muscles during surgical procedures. As shown, the stimulation probe 50 may accommodate within a generally tubularly housing 112 the electrical circuitry of a stimulation control device 22. The stimulation probe 50 is desirably an ergonomic, sterile, single use instrument intended for use during surgical procedures to identify nerves and muscles, muscle attachments, or to contract muscles to assess the quality of surgical interventions or the need for surgical interventions, or to evaluate the function of nerves already identified through visual means. The stimulation probe 50 may be sterilized using ethylene oxide, for example.

The stimulation probe 50 is preferably sized small enough to be held and used by one hand during surgical procedures, and is ergonomically designed for use in either the left or right hand. In a representative embodiment, the stimulation probe 50 may have a width of about 20 millimeters to about 30 millimeters, and desirably about 25 millimeters. The length of the stimulation probe 50 (not including the operative element 110) may be about 18 centimeters to about 22 centimeters, and desirably about 20 centimeters. The operative element 110 may also include an angle or bend to facilitate access to deep as well as superficial structures without the need for a large incision. The operative element 110 will be described in greater detail later. A visual or audio indicator 126 incorporated with the housing 112 provides reliable feedback to the surgeon as to the request and delivery of stimulus current.

Figure 4A:
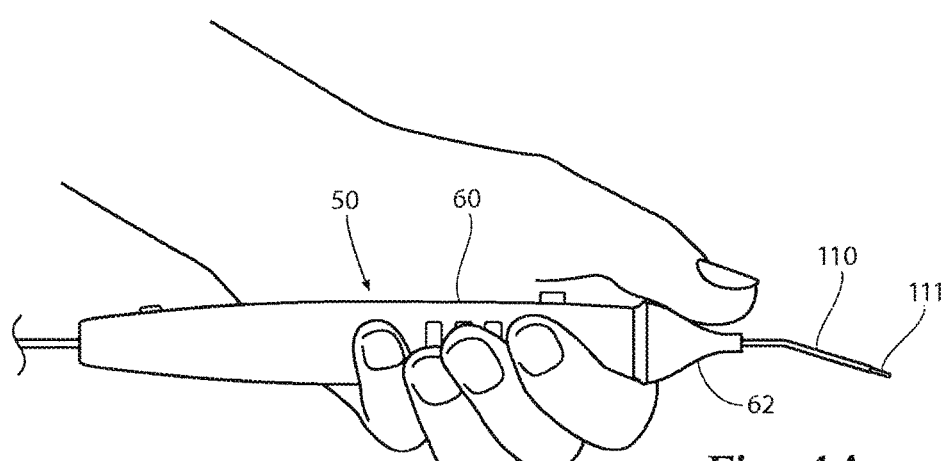
FIG. 4A is a side view of the stimulation probe of FIG. 3c, showing the users hand in a position on the stimulation probe to move the flexible nose cone.
Figure 4B:
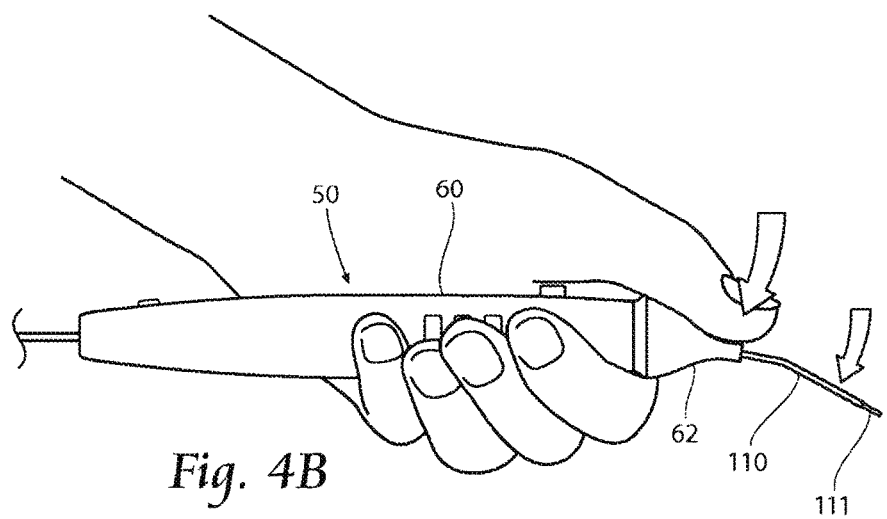
FIG. 4B is a side view of the stimulation probe of FIG. 4A, showing the users hand flexing the flexible nose cone.
Figure 14:
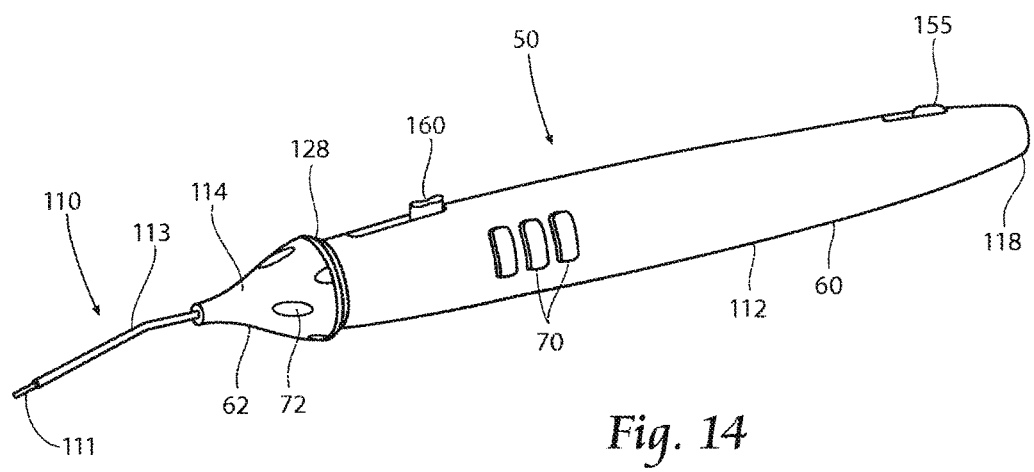
FIG. 14 is a perspective view of the stimulation probe shown in FIG. 3C.

In one embodiment shown in FIGS. 3C and 14, the stimulation probe 50 includes a housing 112 that comprises a gripping base portion 60 and an operative element adjustment portion 62. The operative element 110 extends from the proximal end of the adjustment portion 62. In order to aid the surgeon in the placement of the operative element 110 at the targeted tissue region, the adjustment portion, as will be described as a nose cone 62, may be flexible. This flexibility allows the surgeon to use either a finger or a thumb positioned on the nose cone 62 to make fine adjustments to the position of stimulating tip 111 of the operative element 110 at the targeted tissue region (see FIGS. 4A and 4B). The surgeon is able to grasp the gripping base 60 with the fingers and palm of the hand, and position the thumb on the nose cone 62, and with pressure applied with the thumb, cause the stimulating tip 111 to move while maintaining a steady position of the gripping base portion 62. This flexible nose cone 62 feature allows precise control of the position of the stimulating tip 111 with only the movement of the surgeon's thumb (or finger, depending on how the stimulating probe is held).

Figure 5:
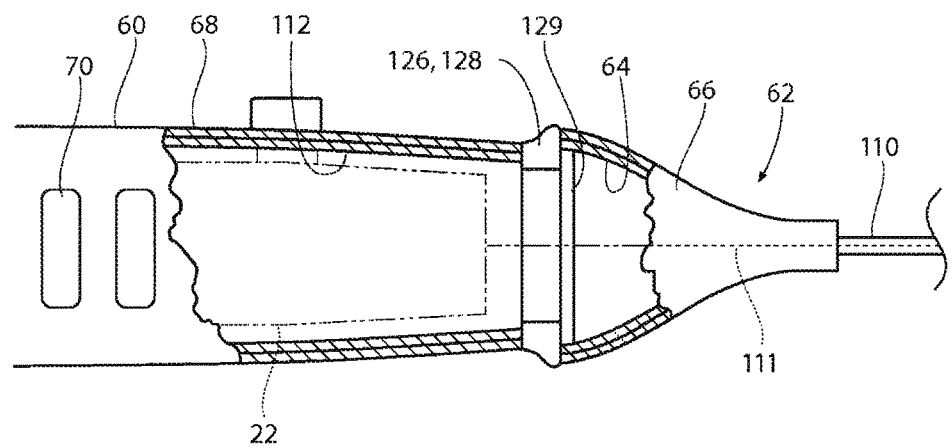
FIG. 5 is a side view with a portion broken away and in section showing elements of the flexible nose cone, the ring indicator, and the gripping base.

The flexible nose cone 62 may comprise a single element or it may comprise at least an inner portion 64 and an outer portion 66, as shown in FIG. 5. In order to facilitate some flexibility of the proximal portion 114 of the stimulation probe 50, the inner portion 64 of the nose cone 62 may be made of a thermoplastic material having some flexibility. One example may be LUSTRAN™ ABS 348, or similar material. The outer portion 66 may comprise a softer over molded portion and may be made of a thermoplastic elastomer material having some flexibility. One example may be VERSAFLEX™ OM 3060-1 from GLS Corp. The nose cone 62 is desirably generally tapered. For example, the nose cone 62 may be rounded, as shown in FIGS. 3A and 3B, or the nose cone may be more conical in shape, as shown in FIG. 3C.

The nose cone 62 may also include one or more features, such as ribs or dimples 72, as shown in FIG. 14, to improve the gripping, control, and stability of the stimulation probe 50 within the surgeon's hand.

The gripping base portion 60 of the housing 112 may also include an overmolded portion 68. The overmolded portion 68 may comprise the full length of the gripping base portion 60, or only a portion of the gripping base 60. The soft overmolded portion 68 may include one or more features, such as dimples or ribs 70, as shown, to improve the gripping, control, and stability of the stimulation probe 50 within the surgeon's hand. The overmolded portion 68 may comprise the same or similar material as the thermoplastic elastomer material used for the outer portion 66 of the flexible nose cone 62.

In one embodiment, the stimulation probe 50 includes a housing 112 that carries an insulated lead 124. The insulated lead 124 connects the operative element 110 positioned at the housing's proximal end 114 to the circuitry 22 within the housing 112 (see FIG. 3A). It is to be appreciated that the insulated lead is not necessary and the operative element 110 may be coupled to the circuitry 22 (see FIG. 3C). The lead 124 within the housing 112 is insulated from the housing 112 using common insulating means (e.g., wire insulation, washers, gaskets, spacers, bushings, and the like). The conductive tip 111 of the operative element 110 is positioned in electrical conductive contact with at least one muscle, or at least one nerve, or at least one muscle and nerve.

As shown, the stimulation probe 50 is mono-polar and is equipped with a single operative element (i.e., electrode) 110 at the housing proximal end 114. A return electrode 130, 131 may be coupled to the stimulation probe 50 and may be any of a variety of electrode types (e.g., paddle, needle, wire, or surface), depending on the surgical procedure being performed. As shown, the various return electrodes 130, 131 are coupled to the housing distal end 118. In an alternative embodiment, the stimulation device 50 itself may be bipolar by including a return electrode in the operative element 110, which precludes the use of a return electrode coupled to the stimulation probe 50.

As shown and described, the stimulation probe 50 may accommodate within the housing 112 the electrical circuitry of a stimulation control device 22. In this arrangement, the stimulation probe 50 may have one or more user operable controls. Two are shown—155 and 160. Power switch 155 serves a dual purpose of turning the stimulation probe 50 ON and OFF (or standby), and also can be stepped to control the stimulation signal amplitude selection within a predefined range (e.g., 0.5, 2.0, and 20 mA). In this configuration, the switch may be a four position switch. Before the first use of the stimulation probe 50, the power switch 155 is in the OFF position and keeps the stimulation probe off. After the stimulation probe 50 has been turned ON—by moving the switch 155 to an amplitude selection—the OFF position now corresponds to a standby condition, where no stimulation would be delivered. In one embodiment, once the stimulation probe 50 has been turned on, it cannot be turned off, it can only be returned to the standby condition and will remain operational for a predetermined time, e.g., at least about seven hours. This feature is intended to allow the stimulation probe 50 to only be a single use device, so it can not be turned OFF and then used again at a later date.

The pulse control device 160 allows for adjustment of the stimulation signal pulse width from a predefined range (e.g., about zero to about 200 microseconds). In one embodiment, the pulse control 160 may be a potentiometer to allow a slide control to increase or decrease the stimulation signal pulse width within the predefined range.

The stimulation pulse may have a non-adjustable frequency in the range of about 10 Hz to about 20 Hz, and desirably about 16 Hz.

Figure 6:
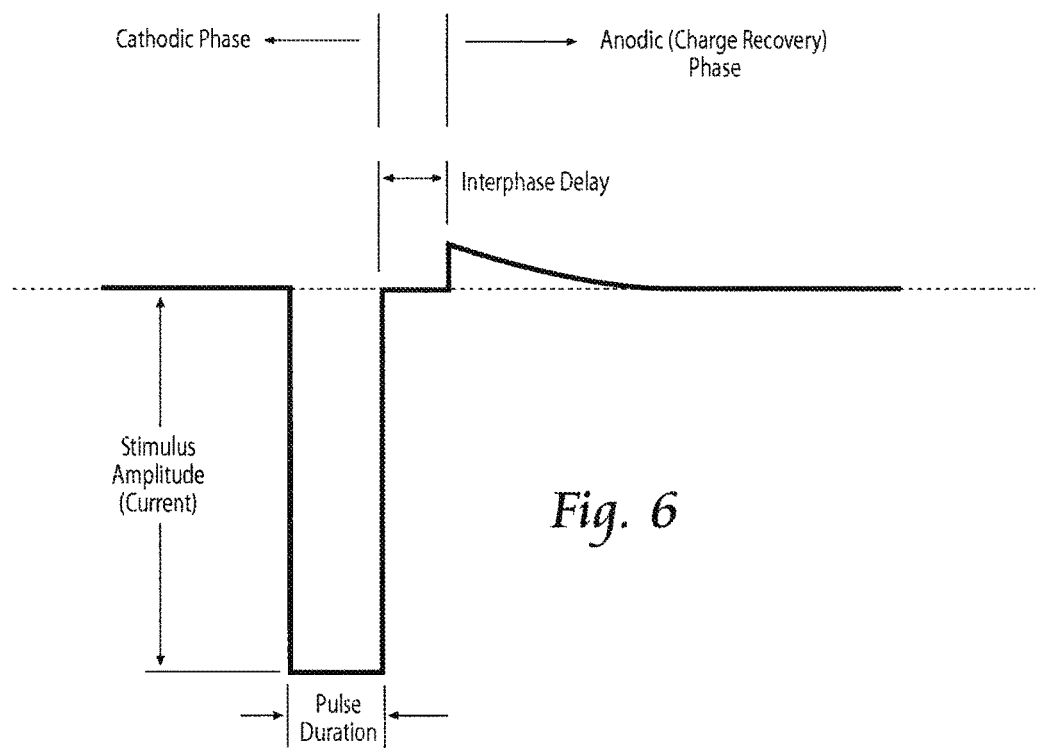
FIG. 6 is a graphical view of a desirable biphasic stimulus pulse output of the stimulation device.

As a representative example, the stimulation pulse desirably has a biphasic waveform with controlled current during the cathodic (leading) phase, and net DC current less than 10 microamps, switch adjustable from about 0.5 milliamps to about 20 milliamps, and pulse durations adjustable from about zero microseconds up to about 200 microseconds. A typical, biphasic stimulus pulse is shown in FIG. 6.

The operative element 110 exits the housing 112 at the proximal end 114 to deliver stimulus current to the excitable tissue. The operative element 110 comprises a length and a diameter of a conductive material, and is desirably fully insulated with the exception of the most proximal end, e.g. about 1.0 millimeters to about 10 millimeters, and desirably about 4 millimeters to about 6 millimeters, which is non-insulated and serves as the stimulating tip or surface (or also referred to as active electrode) 111 to allow the surgeon to deliver the stimulus current only to the intended tissue. The small area of the stimulating surface 111 (the active electrode) of the operative element 110 ensures a high current density that will stimulate nearby excitable tissue. The insulation material 113 may comprise a medical grade heat shrink.

The conductive material of the operative element 110 comprises a diameter having a range between about 0.5 millimeters to about 1.5 millimeters, and may be desirably about 1.0 millimeters. The length of the operative element 110 may be about 50 millimeters to about 60 millimeters, although it is to be appreciated that the length may vary depending on the particular application. As shown, the operative element 110 may include one or more bends to facilitate accurate placement of the stimulating surface 111. In one embodiment, the conductive material of operative element 110 is made of a stainless steel 304 solid wire, although other known conductive materials may be used.

As previously described, in monopolar operation, a return electrode (or indifferent electrode) 130 or 131, for example, provides an electrical path from the body back to the control device 22 within the housing 112. The return electrode 130 (see FIG. 3A) may be placed on the surface of intact skin (e.g., surface electrodes as used for ECG monitoring during surgical procedures) or it might be needle-like 131 (see FIGS. 3B and 3C), and be placed in the surgical field or penetrate through intact skin. The housing's distal end 118 can incorporate a connector or jack 120 which provides options for return current pathways, such as through a surface electrode 130 or a needle electrode 131, having an associated plug 122. It is to be appreciated that a return electrode and associated lead may be an integral part of the stimulation probe 50, i.e., no plug or connector, as shown in FIG. 3C.

Additionally, the device 50 may desirably incorporate a visual or audio indicator 126 for the surgeon. This visual or audio indicator 126 allows the surgeon to confirm that the stimulator 50 is delivering stimulus current to the tissue it is contacting. Through the use of different tones, colors, different flash rates, etc., the indicator 126 (which can take the form, e.g., of a light emitting diode (LED)) allows the surgeon to confirm that the stimulating tip 111 is in place, the instrument is turned ON, and that stimulus current is flowing. Thus the surgeon has a much greater confidence that the failure to elicit a muscle contraction is because of lack of viable nervous tissue near the tip 111 of the stimulator 50 rather than the failure of the return electrode connection or some other instrumentation problem.

As a representative example, in use the indicator 126 may be configured to illuminate continuously in one color when the stimulation probe 50 is turned on but not in contact with tissue. After contact with tissue is made, the indicator 126 may flash (i.e., blink) to indicate that stimulation is being delivered. If the stimulation has been requested, i.e., the stimulation probe has been turned on, but there is no stimulation being delivered because of a lack of continuity between the operative element 110 and the return electrode 130, or an inadequate connection of the operative element 110 or the return electrode 130 to the patient tissue, the indicator 126 may illuminate in a different color, and may illuminate continuously or may flash.

In one embodiment, as can be best seen in FIGS. 3C and 5, the indicator 126 comprises a ring indicator 128 that provides a visual indication around at least a portion, and desirably all of the circumference of the stimulation probe 50 generally near the flexible nose cone 62. The visual ring indicator 128 may be an element of the gripping portion 60, or it may be an element of the flexible nose cone 62, or the ring indicator may positioned between the gripping portion 60 and the flexible nose cone 62. The ring indicator 128 may also include a reflective element 129 to improve and focus the illumination effect of the light emitting source, e.g., one or more LEDs. The ring indicator 128 and the reflective element may be a single component, or more than one component (as can be seen in FIGS. 5 and 15).

Audio feedback also makes possible the feature of assisting the surgeon with monitoring nerve integrity during surgery. The insulated lead 124 connects to the operative element 110 that, in use, is positioned within the surgical field on a nerve distal to the surgical site. Stimulation of the nerve causes muscle contraction distally. The stimulation control device 22 incorporated within the housing 112 may be programmed to provide an audio tone followed by a stimulation pulse at prescribed intervals. The audio tone reminds the surgeon to observe the distal muscle contraction to confirm upon stimulation that the nerve is functioning and intact.

Figure 15:
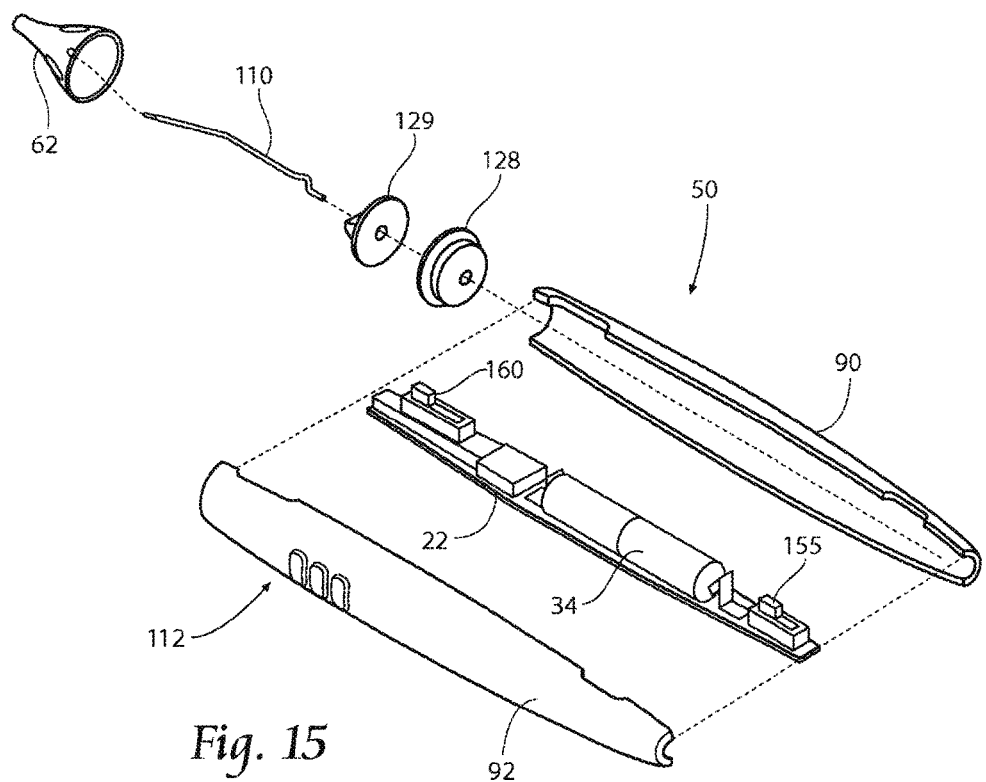
FIG. 15 is an exploded view of the stimulation probe shown in FIG. 14.

FIG. 15 shows an exploded view of a representative stimulation probe 50. As can be seen, the stimulation control device 22 is positioned within the housing 112. A battery 34 is electrically coupled to the control device 22. A first housing element 90 and a second housing element 92 partially encapsulate the control device 22. The ring indicator 128 and the reflective element 129 are coupled to the proximal end of the housing 112. The operative element 110 extends through the nose cone 62 and couples to the control device 22. Desirably, the stimulation probe 50 will be constructed in a manner to conform to at least the IPX1 standard for water ingress.

Figure 7:
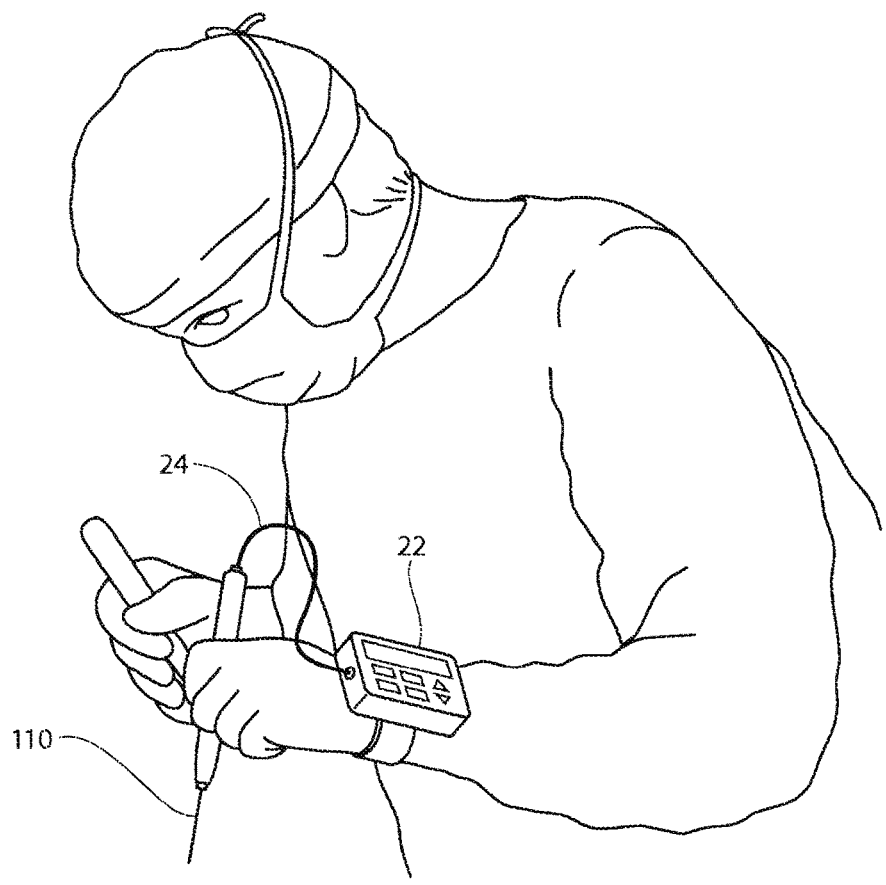
FIG. 7 is a view showing how the geometry of the stimulation control device shown in FIG. 2 aids in its positioning during a surgical procedure.

Alternatively, as FIG. 2 shows, the stimulation control device 22 may be housed in a separate case, with its own input/output (I/O) controls 26. In this alternative arrangement, the stimulation control device 22 is sized small enough to be easily removably fastened to a surgeon's arm or wrist during the surgical procedure, or otherwise positioned in close proximity to the surgical location (as shown in FIG. 7), to provide sufficient audio and/or visual feedback to the surgeon. In this arrangement, the separate stimulation control device 22 can be temporarily coupled by a lead to a family of various medical devices for use.

The present invention includes a method of identifying/locating tissue, e.g., a nerve or muscle, in a patient that comprises the steps of providing a hand-held stimulation probe 50, 100 as set forth above, engaging a patient with the first operative element 110 and the second electrode 130, moving the power switch 155 to an activation position causing a stimulation signal 29 to be generated by the stimulation control device 22 and transmitted to the first operative element 110, through the patient's body to the second electrode 130, and back to the stimulation control device 22. The method may also include the step of observing the indicator 126 to confirm the stimulation probe 50, 100 is generating a stimulation signal. The method may also include the step of observing a tissue region to observe tissue movement or a lack thereof.

B. The Stimulation Control Device

Figure 8:
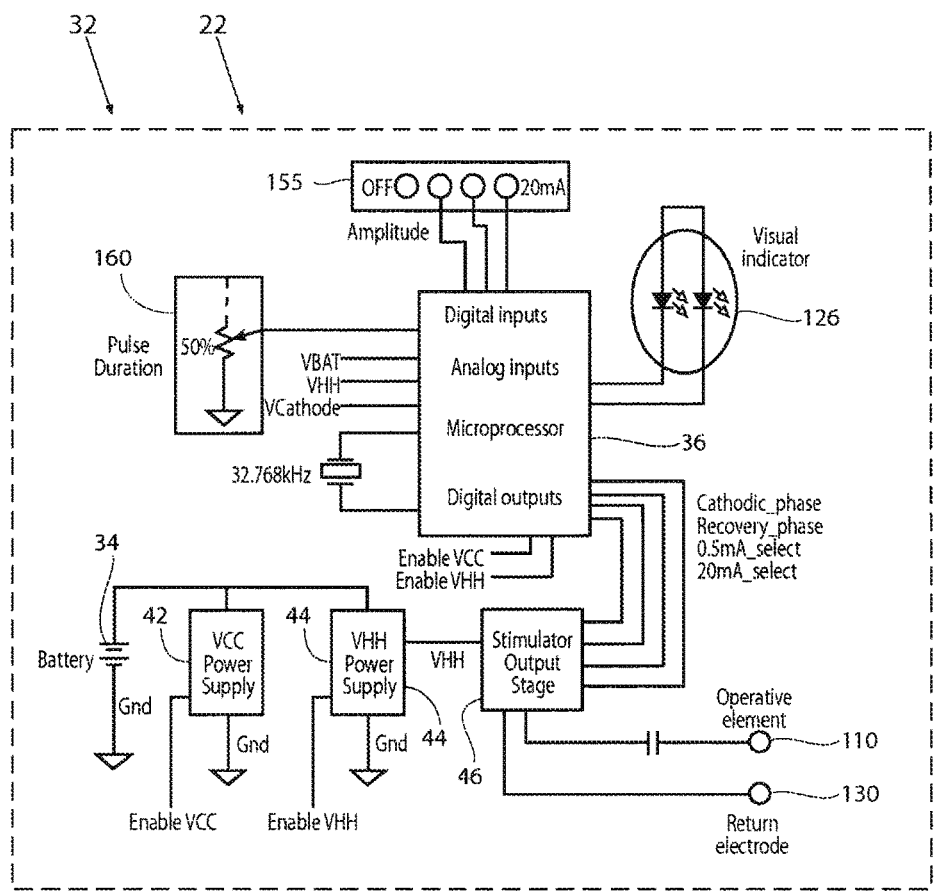
FIG. 8 is a block diagram of a circuit that the stimulation control device shown throughout the Figs. can incorporate.

As FIG. 8 shows, the stimulation control device 22 includes a circuit 32 that generates electrical stimulation waveforms. A battery 34 desirably provides the power. The control device 22 also desirably includes an on-board, programmable microprocessor 36, which carries embedded code. The code expresses pre-programmed rules or algorithms for generating the desired electrical stimulation waveforms using the stimulus output circuit 46 and for operating the visible or audible indicator 126 based on the controls actuated by the surgeon.

In one form, the size and configuration of the stimulation control device 22 makes for an inexpensive device, which is without manual internal circuit adjustments. It is likely that the stimulation control device 22 of this type will be fabricated using automated circuit board assembly equipment and methods.

C. Incorporation with Surgical Devices

A stimulation control device 22 as just described may be electrically coupled through a lead, or embedded within various devices commonly used in surgical procedures (as previously described for the stimulation probe 50).

1. Cutting Device

Figure 9A:
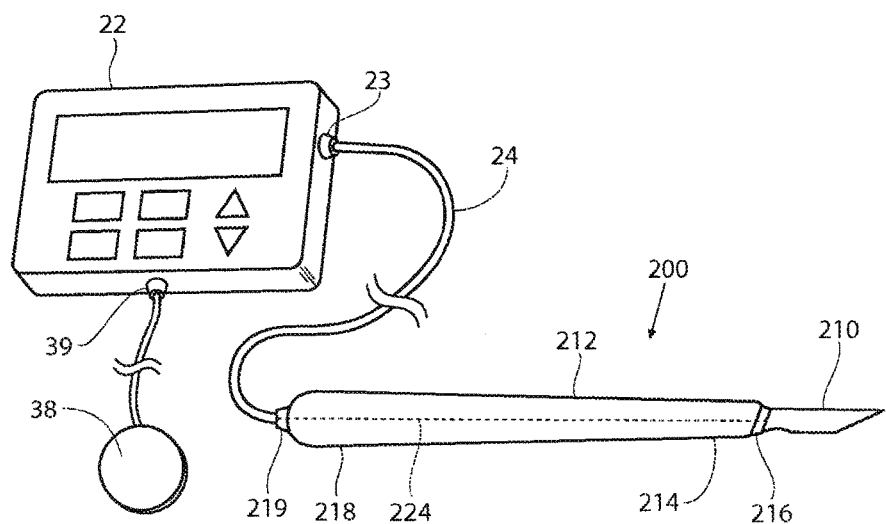
FIGS. 9A and 9B are perspective views showing the stimulation control device in use with a cutting device.
Figure 9B:
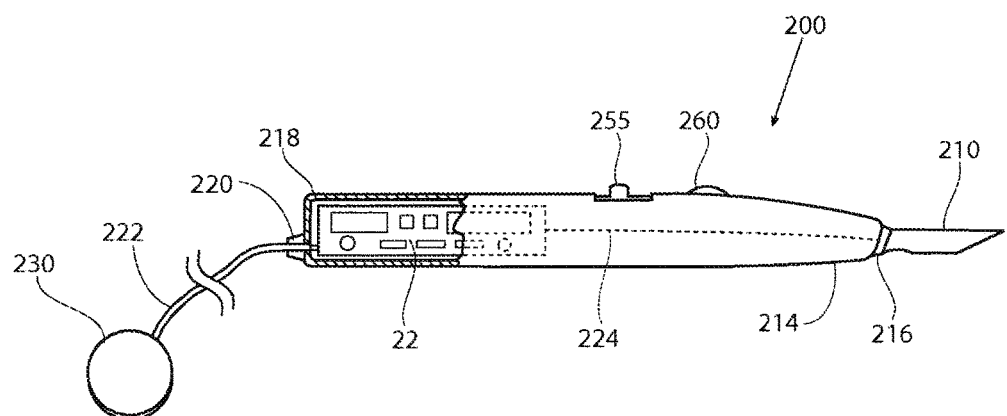

In FIGS. 9A and 9B, a device 200 is shown that incorporates all the features disclosed in the description of the stimulation probe 50, 100, except the device 200 comprises the additional feature of providing an "energized" surgical device or tool. FIG. 9A shows the tool to be a cutting device 200 (e.g., scalpel) removably coupled to a stimulation control device 22.

In the embodiment shown, the cutting device 200 includes a body 212 that carries an insulated lead 224. The insulated lead 224 connects to an operative element, such as electrode 210, positioned at the body proximal end 214 and a plug-in receptacle 219 at the body distal end 118. The lead 224 within the body 212 is insulated from the body 212 using common insulating means (e.g., wire insulation, washers, gaskets, spacers, bushings, and the like).

In this embodiment, the electrode 210 performs the cutting feature (e.g., knife or razor). The electrode 210 performs the cutting feature in electrical conductive contact with at least one muscle, or at least one nerve, or at least one muscle and nerve. The cutting device 200 desirably includes a plug-in receptacle 216 for the electrode 210, allowing for use of a variety of cutting electrode shapes and types (e.g., knife, razor, pointed, blunt, curved), depending on the specific surgical procedure being performed. In this configuration, the lead 224 electrically connects the electrode 210 to the stimulation control device 22 through plug-in receptacle 219 and lead 24.

In one embodiment, the cutting device 200 is mono-polar and is equipped with a single electrode 210 at the body proximal end 214. In the mono-polar mode, the stimulation control device 22 includes a return electrode 38 which functions as a return path for the stimulation signal. Electrode 38 may be any of a variety of electrode types (e.g., paddle, needle, wire, or surface), depending on the surgical procedure being performed. The return electrode 38 may be attached to the stimulation device 22 by way of a connector or plug-in receptacle 39. In an alternative embodiment, the cutting device 200 may be bipolar, which precludes the use of the return electrode 38.

In the embodiment shown in FIG. 9B, the cutting device 200 accommodates within the body 212 the electrical circuitry of the stimulation control device 22. In this arrangement, the cutting device 200 may have at least two operational slide controls, 255 and 260. Power switch 255 serves a dual purpose of turning the stimulation signal to the cutting device 200 on and off, and also is stepped to control the stimulation signal amplitude selection from a predefined range (e.g., 0.5, 2.0, and 20 mA). The pulse control switch 260 allows for adjustment of the stimulation signal pulse width from a predefined range (e.g., zero through 200 microseconds).

At the body distal end 218, a second plug-in receptacle 220 may be positioned for receipt of a second lead 222. Lead 222 connects to electrode 230 which functions as a return path for the stimulation signal when the cutting device 200 is operated in a mono-polar mode.

Additionally, the device 200 may incorporate a visual or audio indicator for the surgeon, as previously described.

The present invention includes a method of identifying/locating tissue, e.g., a nerve or muscle, in a patient that comprises the steps of providing cutting device 200 as set forth above, engaging a patient with the first electrode 210 and the second electrode 230, moving the power switch 255 to an activation position causing a stimulation signal 29 to be generated by the stimulation control device 22 and transmitted to the first electrode 210, through the patient's body to the second electrode 230, and back to the stimulation control device 22. The method may also include the step of observing the indicator 126 to confirm the cutting device 200 is generating a stimulation signal. The method may also include the step of observing a tissue region to observe tissue movement or a lack thereof.

2. Drilling Device

Figure 10A:
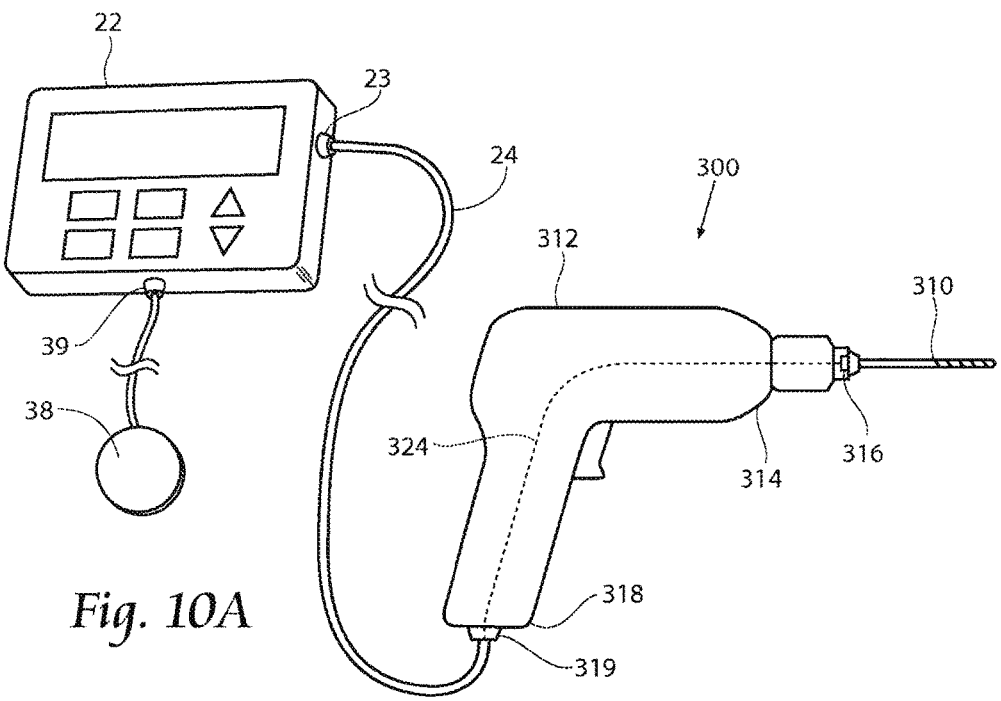
FIGS. 10A and 10B are perspective views showing the stimulation control device in use with a drilling or screwing device.
Figure 10B:
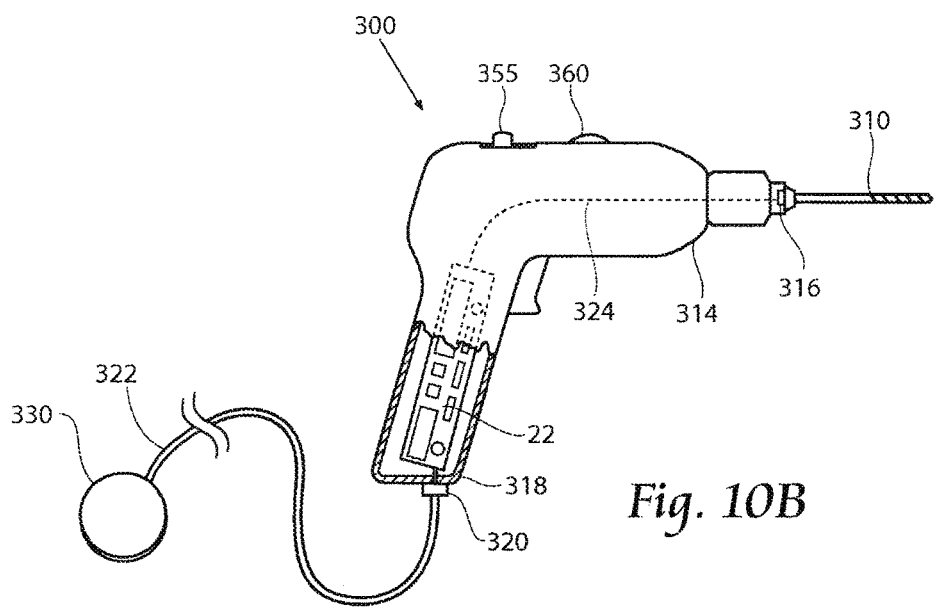

In FIGS. 10A and 10B, a device 300 is shown that incorporates all the features disclosed in the description of the stimulation probe 50, 100, except the device 300 comprises the additional feature of providing an "energized" surgical device or tool, which comprises a drilling device 300. In FIG. 10A is drilling device 300 is removably coupled to a stimulation control device 22.

In the embodiment shown, the drilling device 300 includes a body 312 that carries an insulated lead 324. The insulated lead 324 connects to an operative element, such as electrode 310, positioned at the body proximal end 314 and a plug-in receptacle 319 at the body distal end 318. The lead 324 within the body 312 is insulated from the body 312 using common insulating means (e.g., wire insulation, washers, gaskets, spacers, bushings, and the like).

In this embodiment, the electrode 310 performs the drilling feature. The electrode 310 may also perform a screwing feature as well. The electrode 310 performs the drilling feature in electrical conductive contact with a hard structure (e.g., bone).

The drilling device 300 desirably includes a plug-in receptacle or chuck 316 for the electrode 310, allowing for use of a variety of drilling and screwing electrode shapes and sizes (e.g., ¼ and ⅜ inch drill bits, Phillips and flat slot screw drivers), depending on the specific surgical procedure being performed. In this configuration, the lead 324 electrically connects the electrode 310 to the stimulation control device 22 through plug-in receptacle 319 and lead 324.

In one embodiment, the drilling device 300 is mono-polar and is equipped with a single electrode 310 at the body proximal end 314. In the mono-polar mode, the stimulation control device 22 includes a return electrode 38 which functions as a return path for the stimulation signal. Electrode 38 may be any of a variety of electrode types (e.g., paddle, needle, wire, or surface), depending on the surgical procedure being performed. The return electrode 38 may be attached to the stimulation device 22 by way of a connector or plug-in receptacle 39. In an alternative embodiment, the drilling device 300 may be bipolar, which precludes the use of the return electrode 38.

In FIG. 10B, the drilling device 300 is shown to accommodate within the body 312 the electrical circuitry of the stimulation control device 22. The drilling device 300 may have at least two operational slide controls, 355 and 360. Power switch 355 serves a dual purpose of turning the stimulation signal to the drilling device 300 on and off, and also is also stepped to control the stimulation signal amplitude selection from a predefined range (e.g., 0.5, 2.0, and 20 mA). The pulse control switch 360 allows for adjustment of the stimulation signal pulse width from a predefined range (e.g., zero through 200 microseconds). At the body distal end 318, a second plug-in receptacle 320 may be positioned for receipt of a second lead 322. Lead 322 connects to electrode 330 which functions as a return path for the stimulation signal when the drilling device 300 is operated in a mono-polar mode.

Additionally, the device 300 may incorporate a visual or audio indicator for the surgeon, as previously described.

The present invention includes a method of identifying/locating tissue, e.g., a nerve or muscle, in a patient that comprises the steps of providing a drilling device 300 as set forth above, engaging a patient with the first electrode 310 and the second electrode 330, moving the power switch 355 to an activation position causing a stimulation signal 29 to be generated by the stimulation control device 22 and transmitted to the first electrode 310, through the patient's body to the second electrode 330, and back to the stimulation control device 22. The method may also include the step of observing the indicator 126 to confirm the drilling device 400 is generating a stimulation signal. The method may also include the step of observing a tissue region to observe tissue movement or a lack thereof.

3. Pilot Auger

An additional aspect of the invention provides systems and methods for controlling operation of a family of stimulating devices comprising a stimulation control device electrically coupled to a pilot auger for hard surface rotary probing.

Figure 11A:
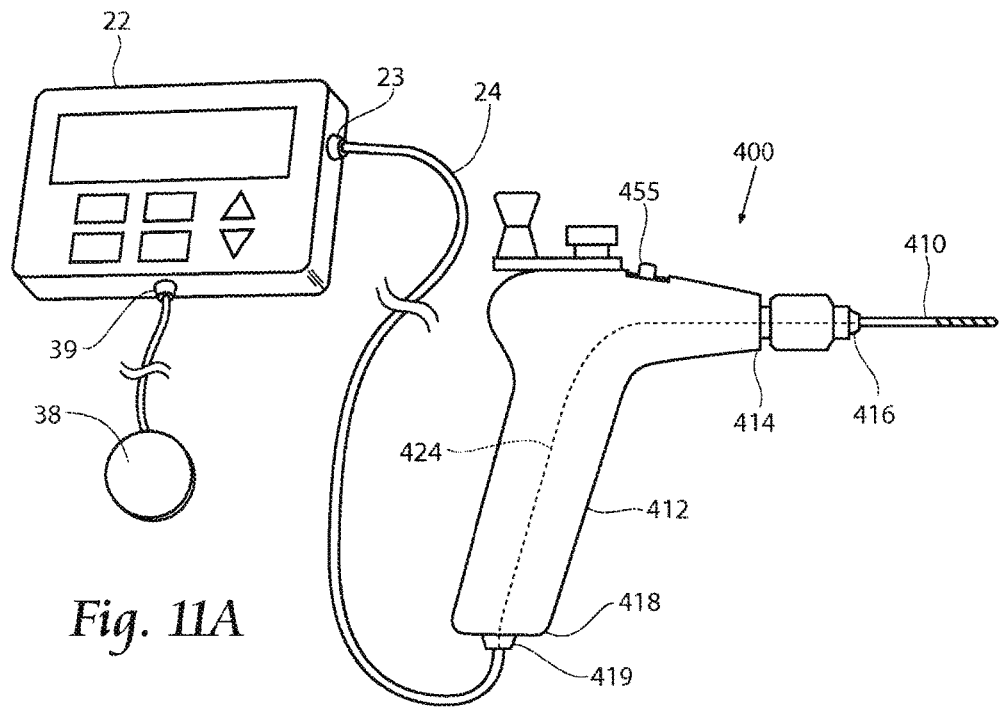
FIGS. 11A and 11B are perspective views showing the stimulation control device in use with a pilot auger device.

This embodiment incorporates all the features disclosed in the description of the stimulation probe 50, 100, except this embodiment comprises the additional feature of providing an "energized" surgical device or tool. FIG. 11A shows a pilot auger device 400 removably coupled to a stimulation control device 22. In the embodiment shown, the pilot auger device 400 includes a body 412 that carries an insulated lead 424. The insulated lead 424 connects to an operative element, such as an electrode 410, positioned at the body proximal end 414 and a plug-in receptacle 419 at the body distal end 418. The lead 424 within the body 412 is insulated from the body 412 using common insulating means (e.g., wire insulation, washers, gaskets, spacers, bushings, and the like). In this embodiment, the electrode 410 performs the pilot augering feature. The electrode 410 performs the pilot augering feature in electrical conductive contact with a hard structure (e.g., bone).

The pilot auger device 400 desirably includes a plug-in receptacle or chuck 416 for the electrode 410, allowing for use of a variety of pilot augering electrode shapes and sizes (e.g., 1/32, 1/16, and 1/8 inch), depending on the specific surgical procedure being performed. In this configuration, the lead 24 electrically connects the electrode 410 to the stimulation control device 22 through plug-in receptacle 419 and lead 24.

In one embodiment, the pilot auger device 400 is mono-polar and is equipped with a single electrode 410 at the body proximal end 414. In the mono-polar mode, the stimulation control device 22 includes a return electrode 38 which functions as a return path for the stimulation signal. Electrode 38 may be any of a variety of electrode types (e.g., paddle, needle, wire, or surface), depending on the surgical procedure being performed. The return electrode 38 may be attached to the stimulation device 22 by way of a connector or plug-in receptacle 39. In an alternative embodiment, the pilot auger device 400 may be bipolar, which precludes the use of the return electrode 38.

Figure 11B:
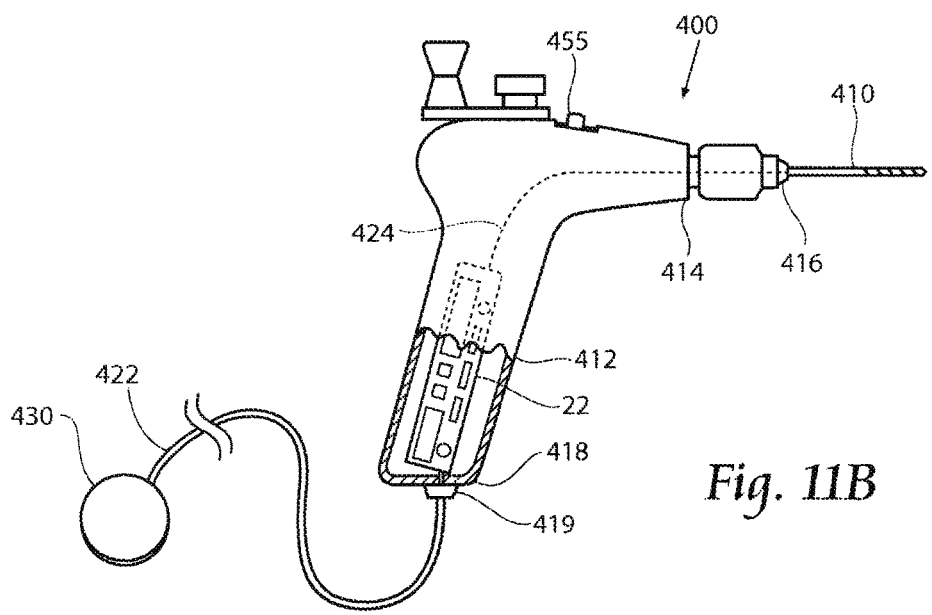

As FIG. 11B shows. the pilot auger device 400 may accommodate within the body 412 the electrical circuitry of the stimulation control device 22. At the body distal end 418, a second plug-in receptacle 420 may be positioned for receipt of a second lead 422. Lead 422 connects to electrode 430 which functions as a return path for the stimulation signal when the pilot auger device 400 is operated in a mono-polar mode.

The pilot auger device 400 includes a power switch 455. When moved to an activation position, a stimulation signal is generated by the stimulation control device 22. Additionally, the device 400 may incorporate a visual or audio indicator for the surgeon, as previously described.

The present invention includes a method of identifying/locating tissue, e.g., a nerve or muscle, in a patient that comprises the steps of providing a pilot auger device 400 as set forth above, engaging a patient with the first electrode 410 and the second electrode 430, moving the power switch 455 to an activation position causing a stimulation signal to be generated by the stimulation control device 22 and transmitted to the first electrode 410, through the patient's body to the second electrode 430, and back to the stimulation control device 22. The method may also include the step of observing the indicator 126 to confirm the pilot auger device 400 is generating a stimulation signal. The method may also include the step of observing a tissue region to observe tissue movement or a lack thereof.

D. Incorporation with Fixation Devices

An additional aspect of the invention provides systems and methods for controlling operation of a family of stimulating devices comprising a stimulation control device electrically coupled to a fixation device or a wrench or screwdriver for placing the fixation device. A fixation device (e.g., orthopedic hardware, pedicle screws) is commonly used during spinal stabilization procedures (fusion), and internal bone fixation procedures.

Figure 12A:
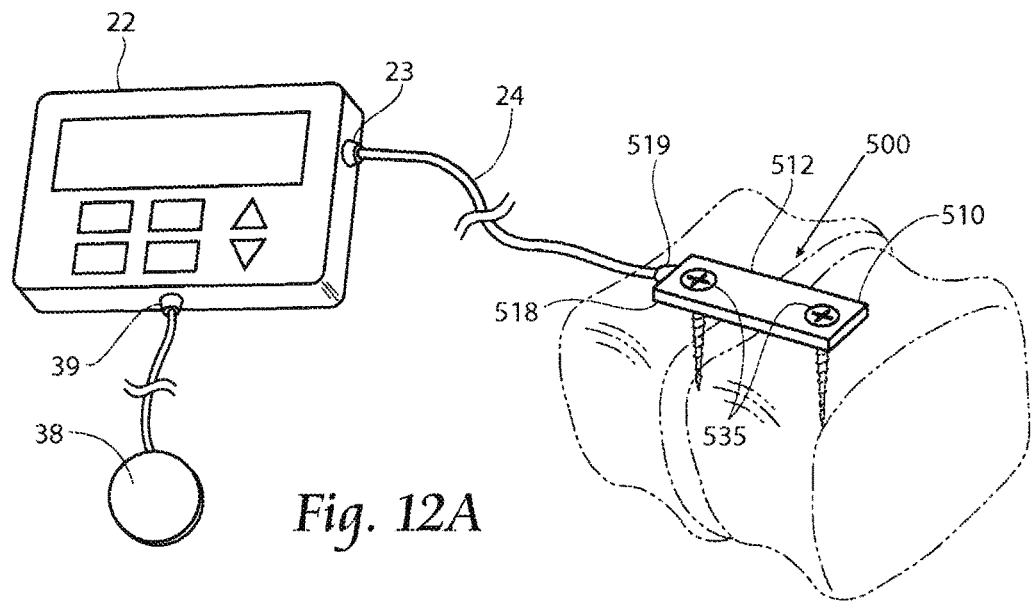
FIGS. 12A and 12B are perspective views showing the stimulation control device in use with a fixation device.

This embodiment incorporates all the features disclosed in the description of the stimulation probe 50, 100, except this embodiment comprises the additional feature of providing an "energized" fixation device or tool. FIG. 12A shows a fixation device 500 removably coupled to a stimulation control device 22. In the embodiment shown, the fixation device 500 includes a rectangularly shaped body 512 that also serves as an operative element, such as electrode 510. The fixation device 500 may take on an unlimited number of shapes as necessary for the particular procedure taking place. Pedicle screws 535 may be used to secure the fixation device to the bony structure. The electrode 510 performs the fixation feature in electrical conductive contact with a hard structure (e.g., bone).

The fixation device 500 or wrench or screwdriver for placing the fixation device desirably includes a plug-in receptacle 519. The fixation device 500 may take on an unlimited variety of shapes and sizes depending on the specific surgical procedure being performed. In this configuration, the lead 24 electrically connects the electrode 510 to the stimulation control device 22 through plug-in receptacle 519.

In one embodiment, the fixation device 500 is mono-polar and is equipped with the single electrode 510. In the mono-polar mode, the stimulation control device 22 includes a return electrode 38 which functions as a return path for the stimulation signal. Electrode 38 may be any of a variety of electrode types (e.g., paddle, needle, wire, or surface), depending on the surgical procedure being performed. The return electrode 38 may be attached to the stimulation device 22 by way of a connector or plug-in receptacle 39. In an alternative embodiment, the fixation device 500 may be bipolar, which precludes the use of the return electrode 38.

Figure 12B:
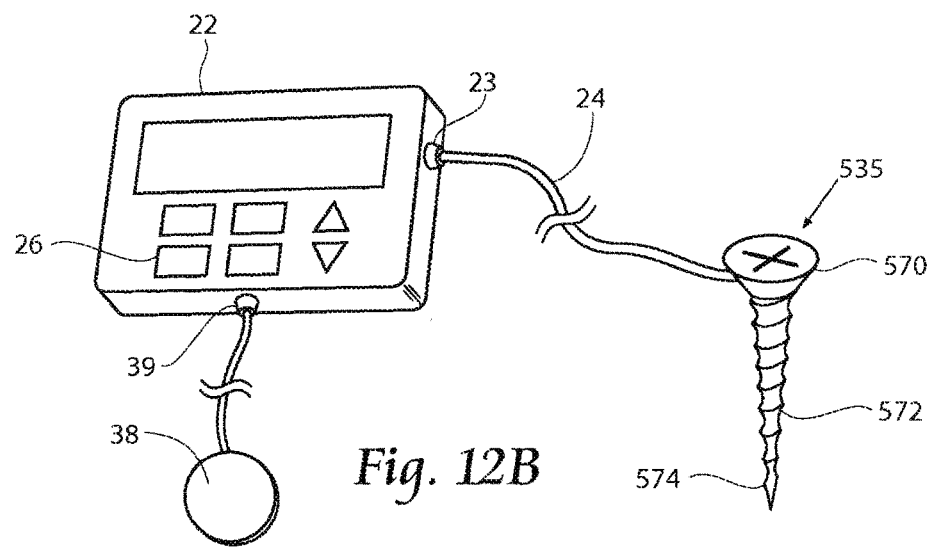
Figure 13:
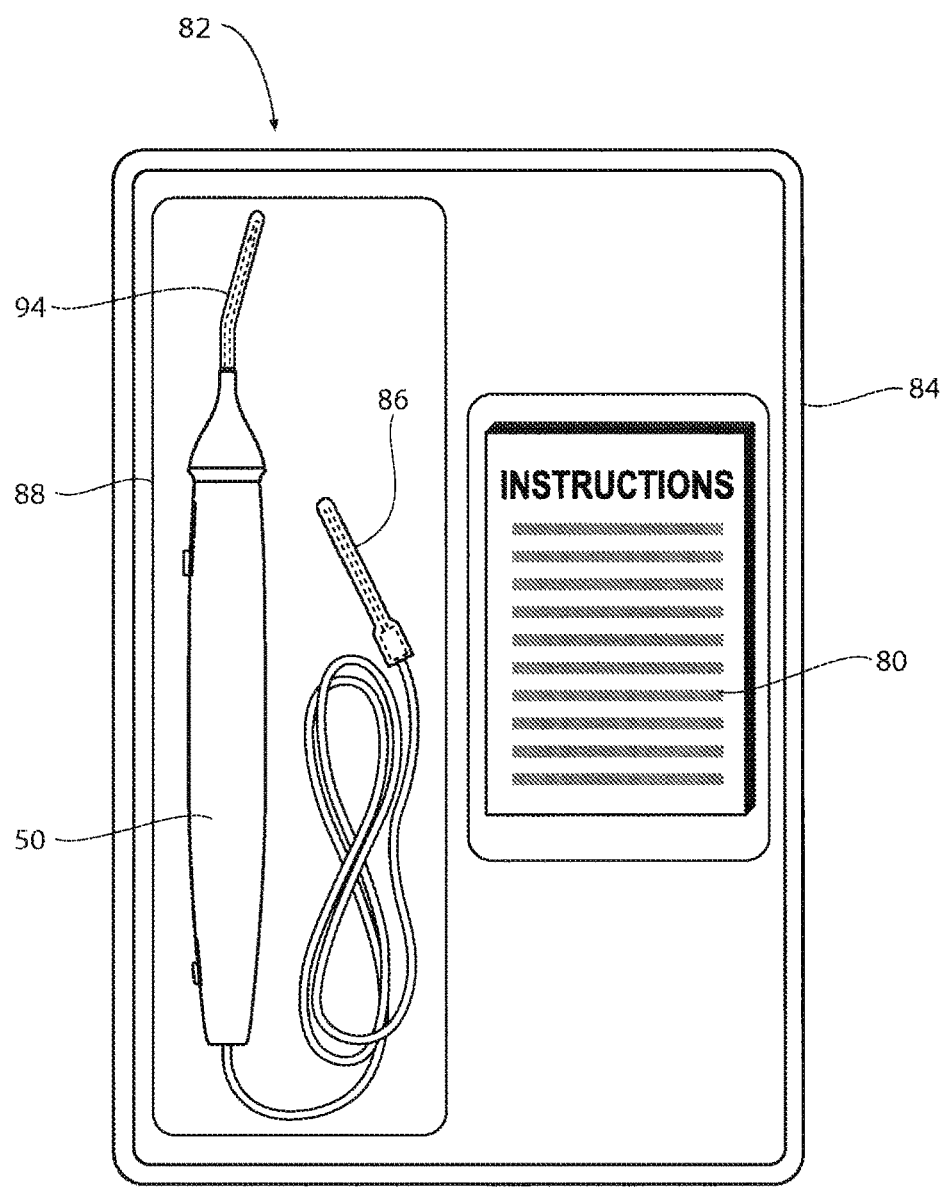
FIG. 13 is a plane view of a kit used in conjunction with the stimulation probe shown in FIG. 3C, and including the stimulation probe and instructions for use.

In yet an additional alternative embodiment (see FIG. 12B), the fixation device may be a pedicle screw 535. The pedicle screw 535 is removably coupled to a stimulation control device 22. In the embodiment shown, the pedicle screw 535 includes a head 570 and a shaft 572, which both serve as an operative element, such as electrode 574. The electrode 574 performs the fixation feature in electrical conductive contact with a hard structure (e.g., bone), as the pedicle screw 535 is being positioned within a bony structure. The lead 24 electrically connects the electrode 574 to the stimulation control device 22, through a break-away connection or other similar electrical connective means. The fixation device 535 may take on an unlimited variety of shapes and sizes depending on the specific surgical procedure being performed.

In the mono-polar mode, the stimulation control device 22 includes a return electrode 38 which functions as a return path for the stimulation signal. Electrode 38 may be any of a variety of electrode types (e.g., paddle, needle, wire, or surface), depending on the surgical procedure being performed. In an alternative embodiment, the fixation device 500 may be bipolar, which precludes the use of the return electrode 38.

The present invention includes a method of identifying/locating tissue, e.g., a nerve or muscle, in a patient that comprises the steps of providing a fixation device 500 as set forth above, engaging a patient with the first electrode 510 and the second electrode 38, turning power on to the stimulation control device 22 through the I/O controls 26, causing a stimulation signal 29 to be generated by the stimulation control device 22 and transmitted to the first electrode 510, through the patient's body to the second electrode 38, and back to the stimulation control device 22. The method may also include the step of observing the indicator 126 to confirm the fixation device 500 is generating a stimulation signal. The method may also include the step of observing a tissue region to observe tissue movement or a lack thereof.

IV. Technical Features

The stimulation control device 22, either alone or when incorporated into a stimulation probe or surgical device, can incorporate various technical features to enhance its universality.

A. Small Size

According to one desirable technical feature, the stimulation control device 22 can be sized small enough to be held and used by one hand during surgical procedures, or to be installed within a stimulation probe or surgical device. The angle of the stimulating tip facilitates access to deep as well as superficial structures without the need for a large incision. Visual and/or audible indication incorporated in the housing provides reliable feedback or status to the surgeon as to the request and delivery of stimulus current.

According to an alternative desirable technical feature, the stimulation control device 22 may also be sized small enough to be easily removably fastened to a surgeon's arm or wrist during the surgical procedure, or positioned in close proximity to the surgical location (as shown in FIG. 7), to provide sufficient audio and/or visual feedback to the surgeon.

B. Power Source

According to one desirable technical feature, power is provided by one or more primary batteries 34 for single use positioned inside the housing and coupled to the control device 22. A representative battery 34 may include a size "N" alkaline battery. In one embodiment, two size "N" alkaline batteries in series are included to provide a 3 volt power source. This configuration is sized and configured to provide an operating life of at least seven hours of operation—either continuous or intermittent stimulation.

C. The Microprocessor/Microcontroller

According to one desirable technical feature, the stimulation control device 22 desirably uses a standard, commercially available micro-power, flash programmable microcontroller 36. The microcontroller 36 reads the controls operated by the surgeon, controls the timing of the stimulus pulses, and controls the feedback to the user about the status of the instrument (e.g., an LED with 1, 2, or more colors that can be on, off, or flashing).

The microcontroller operates at a low voltage and low power. The microcontroller send low voltage pulses to the stimulus output stage 46 that converts these low voltage signals into the higher voltage, controlled voltage, or controlled current, stimulus pulses that are applied to the electrode circuit. This stimulus output stage 46 usually involves the use of a series capacitor to prevent the presence of DC current flow in the electrode circuit in normal operation or in the event of an electronic component failure.

V. Representative Use of a Stimulation Probe

The stimulation probe 50, 100, as described, make possible the application of a stimulation signal at sufficiently high levels for the purposes of locating, stimulating, and evaluating nerve or muscle, or both nerve and muscle integrity in numerous medical procedures, including, but not limited to, evaluating proximity to a targeted tissue region, evaluating proximity to a nerve or to identify nerve tissue, evaluating if a nerve is intact (i.e., following a traumatic injury) to determine if a repair may be needed, evaluating muscle contraction to determine whether or not the muscle is innervated and/or whether the muscle is intact and/or whether the muscle is severed, and evaluating muscle and tendon length and function following a repair or tendon transfer prior to completing a surgical procedure.

Instructions for use 80 are desirably included in a kit 82 along with a stimulation probe 50. The kit 82 can take various forms. In the illustrated embodiment, kit 82 comprises a sterile, wrapped assembly. A representative kit 82 includes an interior tray 84 made, e.g., from die cut cardboard, plastic sheet, or thermo-formed plastic material, which hold the contents. Kit 82 also desirably includes instructions for use 80 for using the contents of the kit to carry out a desired therapeutic and/or diagnostic objectives.

The instructions 80 guide the user through the steps of unpacking the stimulation probe 50, positioning the electrodes, and disposing of the single use disposable stimulator 50. Representative instructions may include, but are not limited to:

(1) Remove the stimulation probe 50 from sterile package 88.

(2) Remove cover 94 (e.g., a silicone cover) from the operative element 110.

(3) Remove protective cover 86 from the return electrode 131.
(4) Position the return electrode 131 in contact with the patient such that:
   (a) The return electrode is desirably positioned in an area remote from the area to be stimulated;
   (b) The return electrode is desirably not positioned across the body from the side being stimulated; and
   (c) The return electrode is desirably not in muscle tissue.
(5) Turn the stimulation probe 500N by moving the power switch 155 from OFF to the 0.5 mA setting (or greater).
(6) The stimulation probe 50 desirably is turned ON before the operative element 110 makes contact with tissue.
(7) The indicator 126 will be illuminated yellow (for example) continuously if the stimulation probe 50 is ON, but not in contact with tissue.
(8) Contact tissue with the operative element 110.
(9) Adjust the pulse control 160 gradually to increase the level of stimulation.
(10) The indicator 126 will flash yellow indicating that stimulation is being delivered.
(11) A flashing red (for example) indicator 126 means that stimulation has been requested, but no stimulation is being delivered because of inadequate connection of the operative element 110 or the return electrode 131 to the patient tissue.
(12) Check the return electrode contact and position, and check the operative element 110 contact and position.
(13) Placing the power switch 155 to the off/standby position will stop stimulation and the visual indictor 126 will be illuminated yellow continuously.
(14) Placing the pulse control 160 at the minimum position will stop stimulation and the visual indictor 126 will be illuminated yellow continuously.
(15) A low/depleted battery 34 will cause the stimulation probe 50 to automatically turn OFF and the visual indicator 126 will not be illuminated.
(16) No further use of the stimulator 50 will be possible.
(17) At end of use, move the power switch 155 to the off/standby position and move the pulse control 160 to the minimum position.
(18) Cut off and dispose of the return electrode 131 in an appropriate sharps/biohazard container.
(19) Dispose of the stimulation probe 50 per hospital or facility guidelines.

In an embodiment shown in FIGS. 16-22, the system may include a bipolar stimulation device as described further below.

The System

Figure 16:
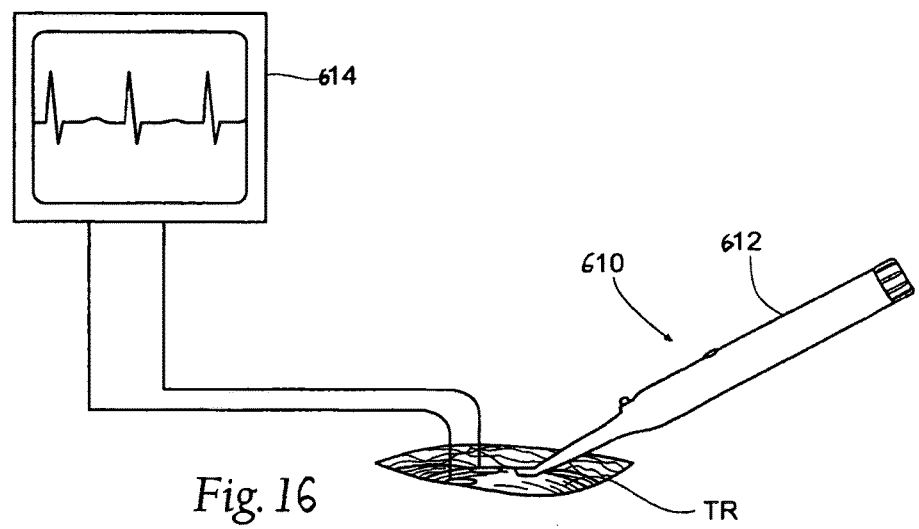
FIG. 16 is a diagrammatic view of a system for differentiating and/or identifying tissue regions locally innervated by targeted nerves.

FIG. 16 shows a system 610 for differentiating and/or identifying within a tissue region TR the presence of a targeted nerve fiber or branch. The system 610 includes a first system 612 for generating and applying a stimulation current to tissue in the region TR of the targeted nerve fiber or branch. The system 610 also includes a second system 614 for sensing the presence or absence of an anticipated physiologic response to the application of the electrical stimulation current. The presence of the anticipated physiologic response differentiates and/or identifies within a tissue region TR the presence of a targeted nerve fiber or branch. Once differentiated and identified, the targeted nerve fiber or branch can be manipulated for desired diagnostic and/or therapeutic reasons.

A. The First Device

Figure 18A:
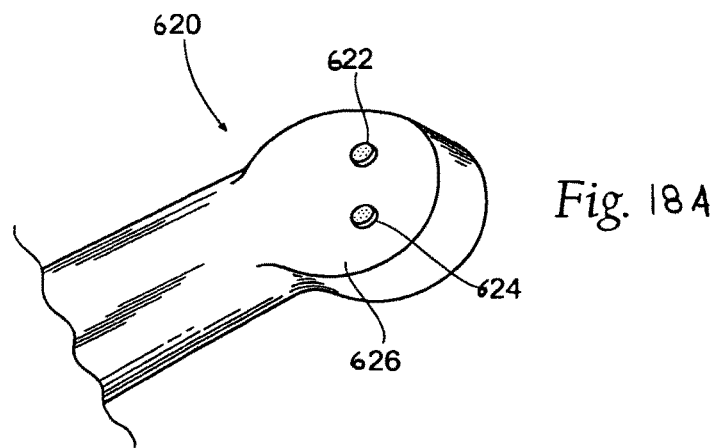
FIG. 18A is an enlarged view of one embodiment of a bipolar electrode array that the device shown in FIG. 17A or 17B may carry at its distal end.
Figure 18B:
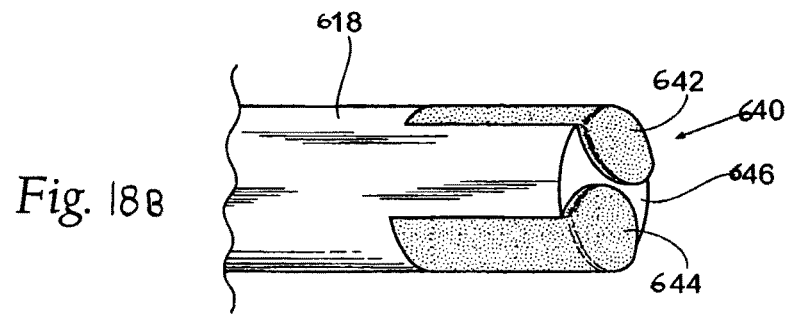
FIG. 18B is an enlarged view of an additional embodiment of a bipolar electrode array that the device shown in FIG. 17A or 17B may carry at its distal end.
Figure 18C:
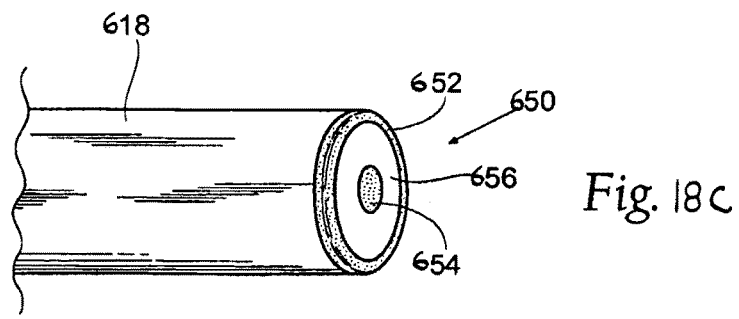
FIG. 18C is an enlarged view of an additional embodiment of a bipolar ring electrode array that the device shown in FIG. 17A or 17B may carry at its distal end.
Figure 19:
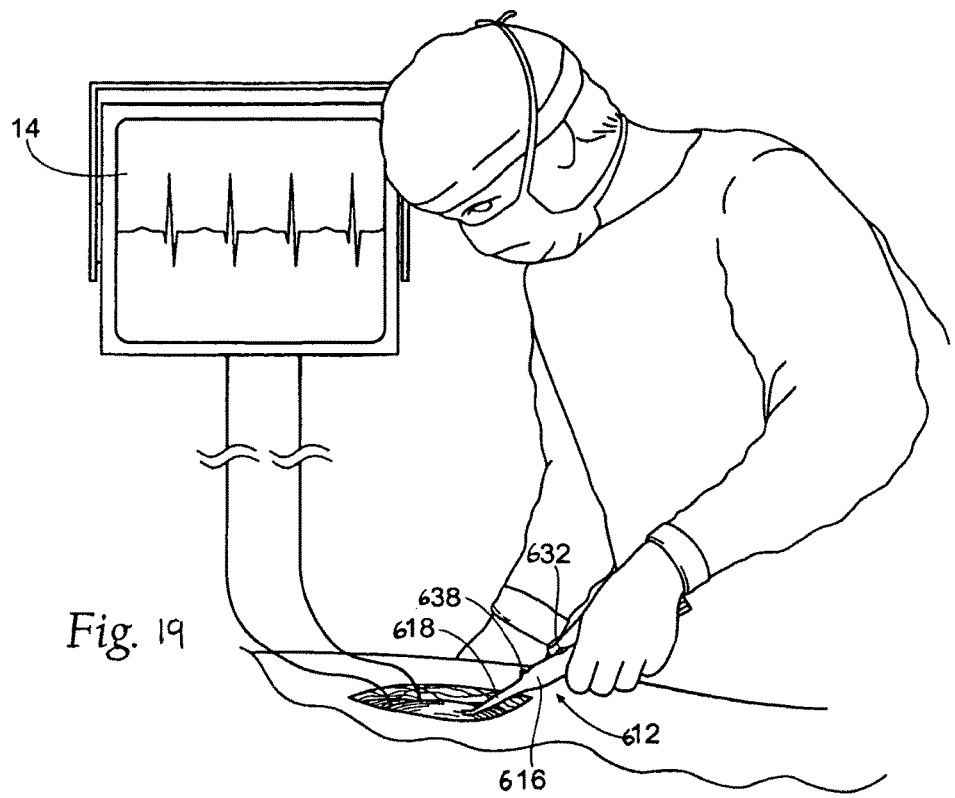
FIG. 19 is a representative view of a clinician manipulating the device shown in FIG. 17A in association with the system shown in FIG. 16.

As FIGS. 17A to 19 show, the first system 612 includes a handle 616, which is preferably sized small enough to be held and used like a flashlight or screwdriver, allowing the thumb to push a button to control the application of stimulus current (see FIG. 19). The handle 616 carries an insulated probe 618. The probe 618 carries, at its distal end, an electrode assembly 620 (see FIG. 18A). The first system 612 is preferably a sterile, single use instrument.

In a representative embodiment, the handle 616 is cylindrical in shape and has a maximum diameter at its proximal end of about 25 mm. The handle 616 tapers from proximal end to distal end to a lesser diameter of about 10 mm. In a representative embodiment, the length of the handle 616 is about 17 cm.

In a representative embodiment, the probe 618 extends about 8 cm from the distal end of the handle 616 and includes an electrode assembly 620 at its distal end. In a representative embodiment, the probe 618 has a diameter of about 10 mm.

The electrode assembly 620 (see FIG. 18A) is sized and configured for accurate identification of tissue regions innervated by targeted nerves. The electrode assembly 620 may be configured to resemble something like a dental mirror and may have a diameter in the range of about 10 mm to about 15 mm. The assembly 620 may be somewhat offset (e.g., 10 degrees to 50 degrees), from the probe 618 to provide ease of use and a more ergonomic configuration. The electrode assembly 620 may comprise a bipolar array of two contacts 622 and 624 exposed on the distal face 626 of the probe 618. The contacts 622 and 624 may have a diameter in the range of about 1 (one) mm to about 3 mm and may project off the distal face by 1 (one) mm or less. The spacing between the contacts 622 and 624 on the distal face 626 may be about 1 (one) mm to about 4 mm. The edges of the contacts 622 and 624 are desirably rounded, so as not to injure tissue. The small area of the contacts 622 and 624 ensures a high current density that will stimulate nearby excitable tissue.

It is to be appreciated that other configures for an electrode assembly may be possible. For example, FIGS. 18B and 18C show two additional possible configurations. FIG. 18B shows an electrode assembly 640 having contacts 642 and 644 exposed on the distal face 646 of the probe 618. The contacts 642 and 644 are circumferentially spaced 180-degrees apart. As shown, the contacts 642 and 644 are exposed on the distal face 646 of the probe 618, each occupying about 90-degrees to about 95-degrees of the circumference of the distal face 646 of the probe 618. The contacts 642 and 644 also desirably extend proximally along the probe for about 5 mm, as well as project a short distance beyond the distal face 646 of the probe 618, e.g., 1 mm. Spacing between the contacts 642 and 644 on the distal face 646 may be about 1 (one) mm to about 4 mm. The edges of the contacts 642 and 644 are desirably rounded, so as not to injure tissue. FIG. 3C shows a ring electrode assembly having an outer contact 652 and an inner contact 654 exposed on the distal face 656 of the probe 618. The outer contact 652 may also extend proximally along the probe.

The contacts 622 and 624 (and their alternative embodiments) can comprise, e.g., stainless steel, silver, platinum, or platinum treated with platinum black. The probe 618 comprises, especially at its distal face 626, a plastic material that is preferably poorly wetted by blood, saline, and body fluids, so as to minimize the risk of passing current through the fluid pathway when direct tissue contact is not present. The probe 618 is insulated from the handle 616 using common insulating means (e.g., wire insulation, washers, gaskets, spacers, bushings, and the like).

Alternatively, a monopolar arrangement can be used. In this arrangement, a return electrode (or indifferent electrode) must be provided to provide an electrical path from the body back to the instrument. The return electrode may be placed on the surface of intact skin (e.g., surface electrodes, such as used for ECG monitoring during surgical procedures) or it might be needle-like and be placed in the surgical field or penetrate through intact skin.

Figure 17A:
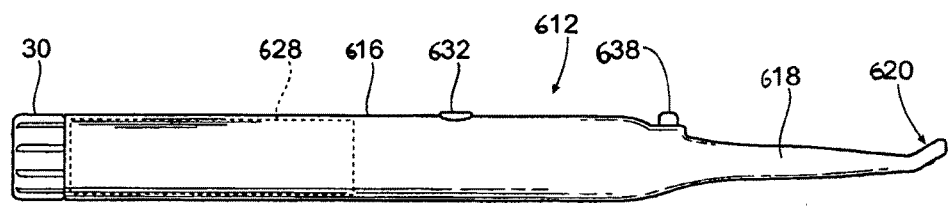
FIG. 17A is side view of a device used in conjunction with the system shown in FIG. 1 for generating and applying a stimulation current to tissue in the region of the targeted nerve fiber or branch.
Figure 17B:
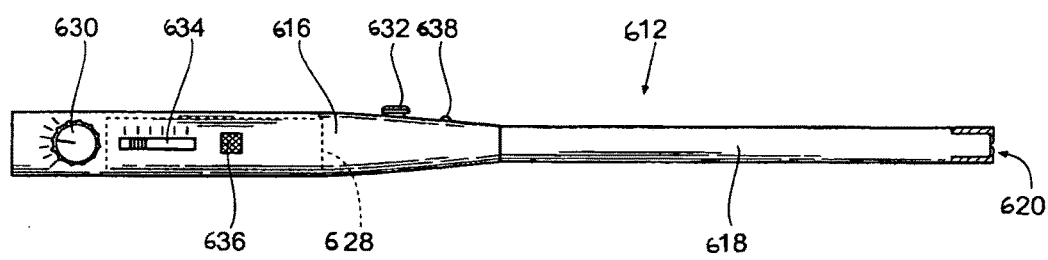
FIG. 17B is side view of an alternative embodiment of the device shown in FIG. 2A, and having separate amplitude and duration selection switches.

An electrical stimulation control circuitry 628 is carried within the handle 616 (see FIGS. 17A and 17B). The control circuitry 628 generates a stimulation current which is applied through the contacts 622 and 624. The control circuitry 628 is powered by a primary battery (for single use applications) located within the handle 616. If the instrument is not intended for single use, the battery can be rechargeable.

The control circuitry 628 desirably includes an on-board, programmable microprocessor, which carries embedded code. The code expresses pre-programmed rules or algorithms for generating the desired electrical stimulation waveforms. In a representative embodiment, the stimulus frequency is 20 Hz, (although the frequency may be adjustable, e.g., 3 Hz to 100 Hz), and the waveform comprises a charge balanced biphasic waveform (i.e., no net DC current flow).

Other operating parameters of the control circuitry 628 can be regulated by controls conveniently carried on the handle 616.

In the illustrated embodiment (see FIG. 17A), stimulus amplitude and the stimulus pulse duration are adjusted by a rotary switch 630 or wheel near or on the proximal end of the handle 616. The rotary control switch 630 desirably has labeling to identify multiple setting options. For example, the first few settings may include different amplitudes each with the same fixed pulse duration. Additional settings may provide a range of selectable settings that include specific combinations of amplitudes and pulse durations. The rotary control switch 630 also desirably has detents that gives the clinician good tactile feedback when moving from one setting to the next. The range of stimulus settings labeled can comprise, e.g., OFF, STANDBY, 1.5 mA at 100 µsec, 3 mA at 100 µsec, 5 mA at 100 µsec, 5 mA at 300 µsec, and 10 mA at 500 µsec.

A momentary pushbutton 632, e.g., on the side of the housing 616, e.g., for access by a thumb, controls the delivery of the stimulation current through the contacts 622 and 624. The momentary pushbutton 632 allows the first system 612 to be controlled, e.g., stimulation current to be turned on and off, with only one hand. The stimulus current is delivered (at the amplitude/duration set by the rotary switch 630) through the contacts 622 and 624 only if the momentary pushbutton 632 is depressed. If the pushbutton 632 is not depressed, no stimulus current is delivered.

In an alternative embodiment (see FIG. 17B), the stimulus pulse duration may be regulated by an adjustable stepped slide switch 634 on the handle 616. Thus, if the momentary pushbutton 632 is depressed, stimulus current is applied at the regulated amplitude and regulated duration. If the pushbutton 632 is not depressed, no stimulus current is delivered. The slide switch 634 desirably has labeling to identify the pulse duration selected. The slide switch 634 also desirably has detents that gives the clinician good tactile feedback when moving from one pulse duration level to the next. The range of pulse duration settings labeled can comprise, e.g., OFF, 100 µsec, 300 µsec. or 500 µsec. The slide switch 634 could also have a STANDBY position labeled.

Alternatively, if the pulse duration slide switch 634 is not provided, and the pulse duration is not selected via the rotary control switch 630, the stimulus pulse durations can be fixed at a nominal selected duration, e.g., 250 µsec.

The control circuitry 628 desirably includes a light indication, i.e., a light emitting diode LED 638 on the handle, that provides various indications to the clinician. For example, the LED 638 may confirm battery status and stimulator ON/OFF states. Also desirably, the LED 638 may flash green when adequate stimulus is being delivered, and flash red when inadequate stimulus is delivered. In addition, the LED 638 may flash or illuminate only if the current actually delivered is within a desired percentage of the requested amplitude, e.g., within 25% of the requested value. The control circuitry 628 thereby provides reliable feedback to the clinician as to the requested delivery of stimulus current.

In an alternative embodiment, the control circuitry 628 may also generate an audio tone only when the stimulus current is being delivered. The tone is transmitted by an indicator 636 on the handle 616.

Through the use of different tones, colors, different flash rates, etc., the control circuitry 628 can allow the clinician to confirm that the probe is in contact with tissue, the instrument is turned ON, the battery has sufficient power, and that stimulus current is flowing. Thus the clinician has a much greater confidence that the failure to elicit a desired response is because of lack of viable nervous tissue near the tip of the probe rather than the failure of the return electrode connection or some other instrumentation problem.

B. The Second Device

The second system 614 can take various forms, depending upon the physiologic function of the targeted tissue region and the nature and character of the physiologic response anticipated due to the application of the electrical stimulation current by the first system 612.

For example, the electrical stimulation of parasympathetic nerves affecting a respiration activity causes breathing to slow. Therefore, when it is desired to differentiate and/or identify the presence or absence of parasympathetic nerves affecting a respiration activity, a reduction in the breathing rate can be used as the anticipated physiologic response. In this arrangement, the second system 614 can comprise an instrument that monitors breathing. The instrument can comprise, e.g., a chest position sensor and a spirometer box that monitor movements of the chest. The instrument can also comprise a breathing sensor, which is worn around the chest, such as a breathing (stretch) sensor or a stethograph. A decrease in breathing rate detected by the second device indicates that the first device is located at or near parasympathetic nerves.

As another example, the stimulation of parasympathetic nerves affecting heart function increases the resting potential and decreases the rate of diastolic depolarization. Under these circumstances the heart rate slows. Therefore, when it is desired to differentiate and/or identify the presence or absence of parasympathetic nerves affecting heart activity, the heart rate can be used as the anticipated physiologic response. In this arrangement, the second system 614 can comprise an electrocardiography (EKG) instrument.

As another example, the stimulation of parasympathetic nerves affecting digestion (e.g., during the cephalic phase of gastric secretion) mediates reflex gastric secretion. Therefore, when it is desired to differentiate and/or identify the presence or absence of parasympathetic nerves affecting stomach activity, the reduction in the secretion of gastric juice can be used as the anticipated physiologic response. In this arrangement, the second system 614 can comprise instrumentation that senses the secretion of gastric juice.

As another example, the second system 614 can comprise an electromyography (EMG) instrument. The EMG instrument measures nerve impulses within muscles. The EMG system includes electrodes that are placed in the muscles in the tissue region innervated with parasympathetic nerves, and the electronic responses to operation of the first system 612 can be observed using an instrument that displays movement of an electric current (e.g., an oscilloscope). As muscles contract, they emit a weak electrical signal that can be detected, amplified, and tracked as the anticipated physiologic response.

III. Use of the System

In use, the first system 612 is positioned in contact with tissue in a targeted tissue region TR. A clinician may operate the first system 612 with one hand to apply the stimulation current. The clinician's other hand can then be used to make adjustments to the stimulation current as necessary. The second system 614 monitors the physiologic response. The first system 612 is located and relocated (if necessary) until the monitored physiologic response indicated by the second system 614 matches or approximates the anticipated physiologic response. This indicates the presence of the targeted nerve fiber or branch, and the identified location may then be marked. A desired treatment regime can then be performed, e.g., to manipulate the parasympathetic nervous system for therapeutic benefit.

Figure 20:
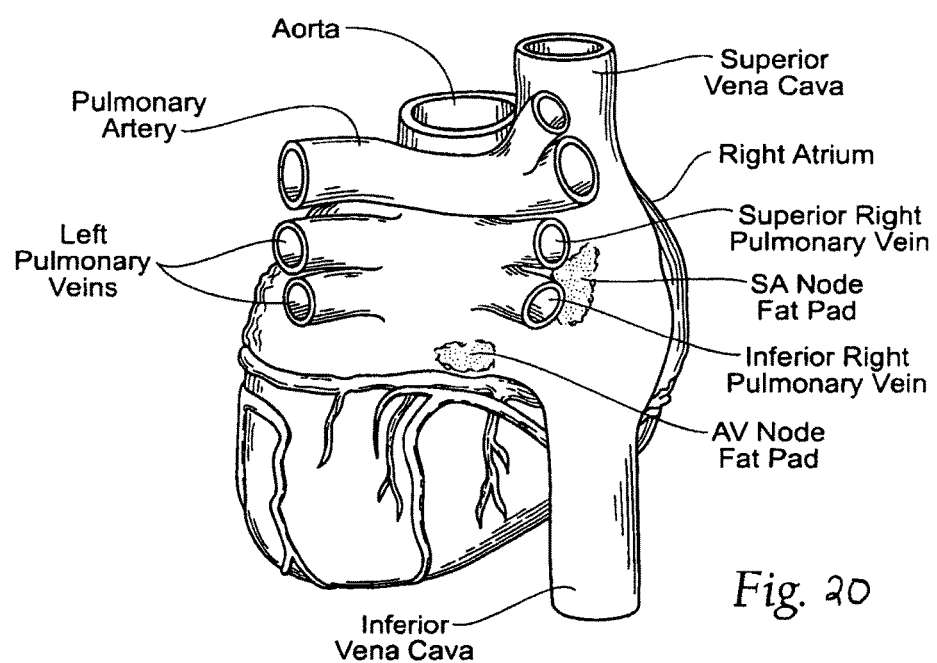
FIG. 20 is an anatomic posterior view of a human heart, showing the location of fat pads innervated by parasympathetic nerves that, when accessed, can provide therapeutic benefits.
Figure 21:
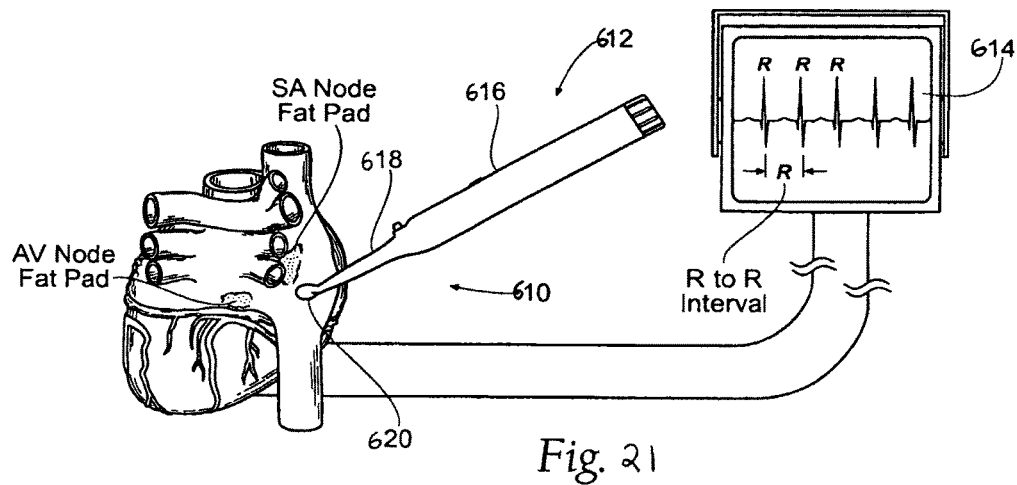
FIGS. 21 and 22 are diagrammatic views of use of the system shown in FIG. 16 for differentiating and/or identifying a fat pad tissue region that is locally innervated by parasympathetic nerves.
Figure 22:
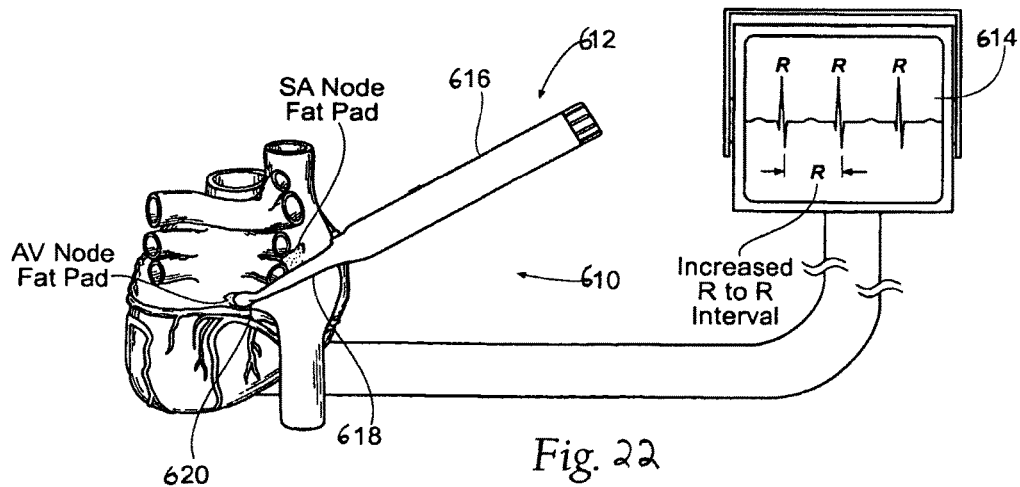

For example, it has been observed that the parasympathetic nervous system of the heart can be manipulated to coordinate cardiac conduction and/or function as relates to atrial fibrillation, without tissue ablation and without interrupting physiologic conduction. It is known that parasympathetic nerve fibers of the vagus nerve can be manipulated to affect atrial cycle length. It is also known that parasympathetic nerve fibers of the vagus nerve selectively innervate the epicardial antrioventricular (AV) node fat pad and the sinoatrial (SA) node fat pad (as FIG. 20 shows).

The system 610 makes possible, e.g., the differentiation and identification of the epicardial AV node fat pad on the surface of the heart, and thereby makes it possible to access the parasympathetic nervous system of the heart at this location for therapeutic benefit.

More particularly, the first system 612 of the system 610 makes possible the application highly localized electrical stimulation on the surface of the heart, while the second system 614 monitors heart rate. The clinician may start the application of the stimulus current at the lowest amplitude setting, and increase the amplitude setting as necessary. Adjustments may be necessary due to the physiological differences of tissue regions from patient to patient. The clinician may also start the application of the stimulus current at something other than the lowest amplitude setting after a visual inspection of the tissue region TR indicates that a higher initial setting may be necessary.

When the first system 612 is applying stimulation and is ultimately located at or near the region of the AV node fat pad (see FIG. 22), the heart rate (monitored by the second system 614, e.g., an EKG instrument) will decrease. An EKG instrument 614 will indicate a decrease in heart rate by an increase in the R-to-R interval observed on EKG (compare the R-to-R interval shown in FIG. 21 to the increased R-to-R interval shown in FIG. 22). The clinician may then stop the application of stimulation current to the tissue region, e.g., the identified AV node fat pad, and observe an increase in the heart rate returning to the original heart rate (a decrease in the R-to-R interval observed on EKG). The clinician may go through the steps of applying stimulation current, observing an increase of the R-to-R interval, stopping the application of stimulation current, and observing a decrease in the R-to-R interval, to confirm the accurate location of the targeted tissue region, e.g., the AV node fat pad. In this way, the system 610 allows a clinician to systematically and accurately locate the AV node fat pad (and other regions selectively innervated by parasympathetic nerves) on the surface of the heart.

Once located, the clinician may use the first system 612 to apply a die or other marker to maintain identification of the AV node fat pad. Alternatively, a separate applicator may be used to apply a die or other marker, or, the clinician may use visual skills along with their finger, for example, to maintain identification of the AV node fat pad. The clinician can then take steps to perturb the parasympathetic nervous system of the heart for therapeutic benefit. For example, by either electrical or non-electrical manipulation of the AV node fat pad located by the system 610, the clinician can treat or prevent uncontrolled atrial fibrillation or perform other desired therapies, or the clinician can apply closed-loop feed-back control algorithms that provide physiologic control of AV nodal rate.

Manipulation of the AV node fat pad located by the system 610 preserves physiologic conduction. With electrical manipulation, its beneficial effects can be turned on and turned off instantaneously, and without attenuation of effect. Manipulation of the AV node fat pad may provide a viable alternative to AV node ablation in the treatment of atrial fibrillation, which does not preserve physiologic conduction and instead consigns patients to pacemaker dependency.

Adapter Designs

In an embodiment, the system 20 may be configured to receive an adapter. The adapter may be configured to connect to a portion of the system 20, such as to a stimulation probe 50. The adapter may provide additional functionality, usability, and control of the stimulation probe 50.

In an embodiment, the adapter may be a bipolar adapter 710, as shown in FIGS. 23-29. The adapter may be configured to attach to a control device 22, such as a stimulation probe 50, to allow the device to function as a bipolar device, having all the functionality of the bipolar device described above.

The bipolar adapter 710 may be used with a monopolar stimulation device to provide more precise stimulation control. Specifically, the bipolar adapter 710 may provide a return element 716, in addition to the primary operative element 110 of the stimulation probe 50, to constrain the stimulation electrical field and direct stimulation to a specific desired location, such as target nerve. The return element 716 may comprise a wire or any other insulated electrical conductor and may include a tip or electrode 718 for making electrical contact with a target tissue.

Figure 23:
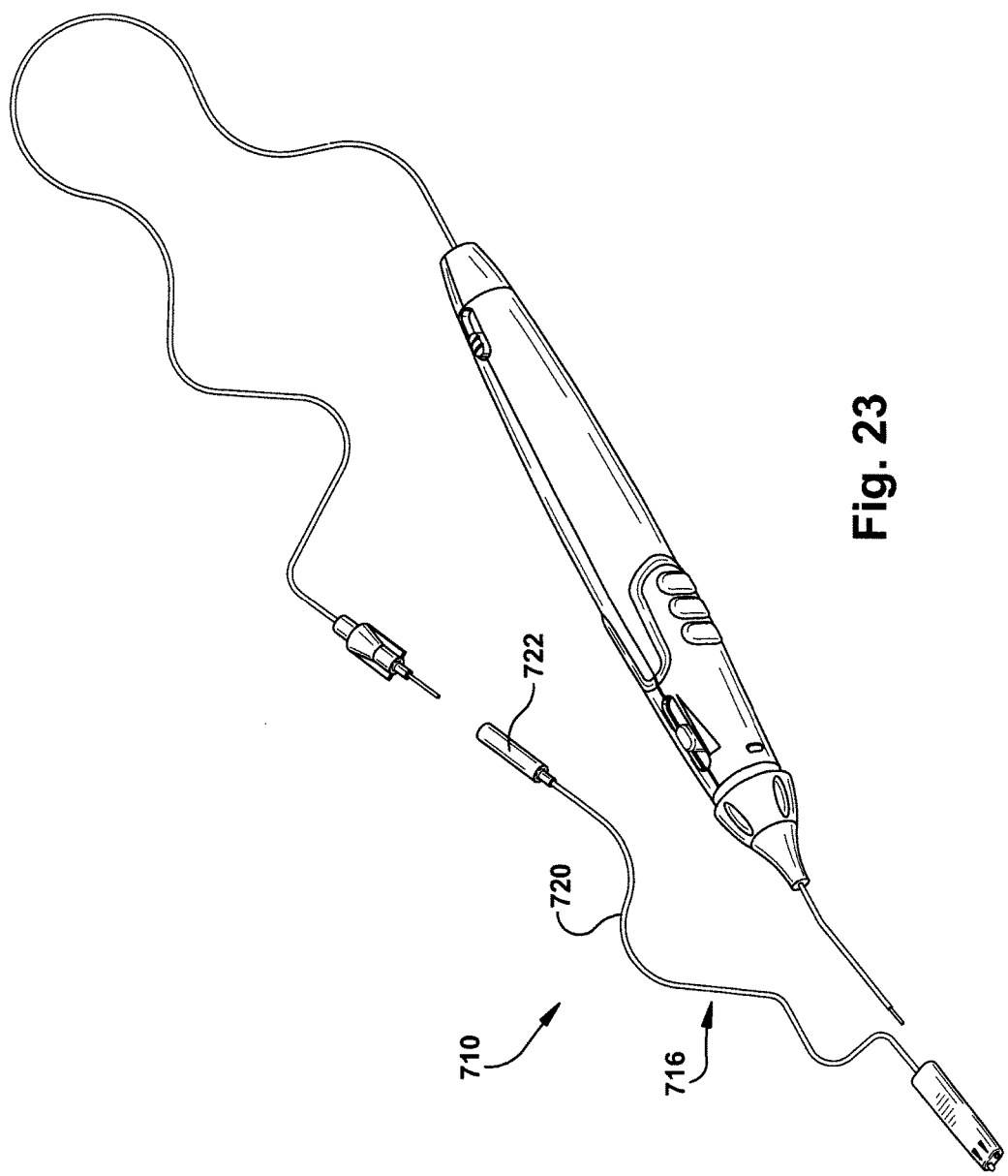
FIG. 23 is a stimulation device connected to a bipolar adapter.
Figure 24:
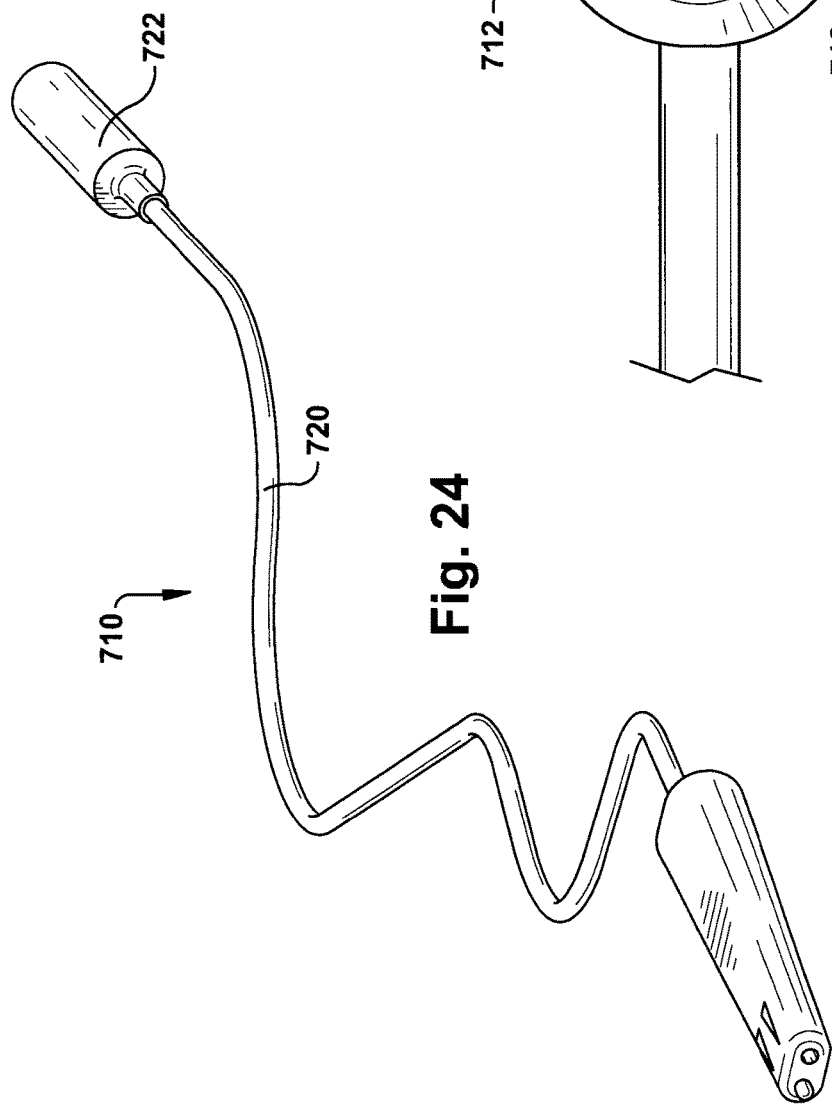
FIG. 24 is a bipolar adapter connector.

In an embodiment, the adapter 710 may include a connector 712. The connector 712 may be any appropriate size and shape, such as generally elongated as shown in FIGS. 23 and 24. The connector 712 may be generally tapered so as not to obstruct a user's view during a procedure. The connector 712 may be configured to connect to the stimulation probe 50. For example, the connector may include an opening 714 to receive a portion of the operative element 110 of the stimulation probe 50 therein. The opening 714 may extend through a portion or the entirety of the connector 712. The opening 714 may be sized and shaped to receive the operative element 110 therein. For example, the operative element 110 may extend through the opening from a first end of the connector 712 and protrude through the opening 714 at the second or opposite end of the connector 712. A conductive portion of the operative element 110 may be exposed to allow electrical current to flow to the target tissue.

The opening 714 may be configured to hold the operative element 110 in place. For example the opening 714 may be tapered to hold the probe in a compression fit. The opening 714 may further be configured to include a set screw or other retaining feature to maintain the operative element 110 at the desired location.

Figure 25:
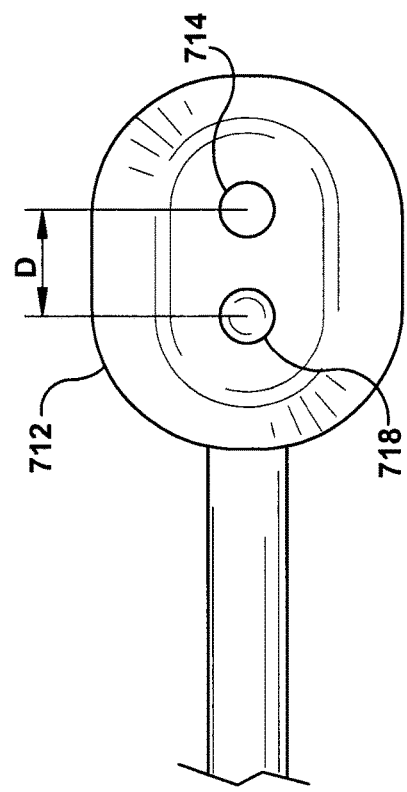
FIG. 25 is a front view of a bipolar connector adapter.

The connector 712 may include the second probe or return element 716. As shown in FIG. 25, the return operative element 716 may be spaced apart a specified distance D from the opening 714. The distance D may be measured from the center of the opening 714 to the center of the return element 716, and may be any appropriate distance, such as 2 millimeters, 1 millimeter, or any other appropriate distance.

The return element 716 may be any appropriate diameter. For example, the stimulation probe 50 operative element 110 may have a diameter of approximately 0.04 inches. The return element 716 may have a smaller diameter, such as 0.02 inches, or any other appropriate diameter.

The bipolar adapter 710 may further include a pigtail wire 720 extending from the connector 710. The pigtail 720 may be any appropriate length and may be configured to be electrically tied to ground or any appropriate circuit. For example, the pigtail 720 may include a connector 722 at one end to receive luer connection or other electrical connection.

Figure 26:
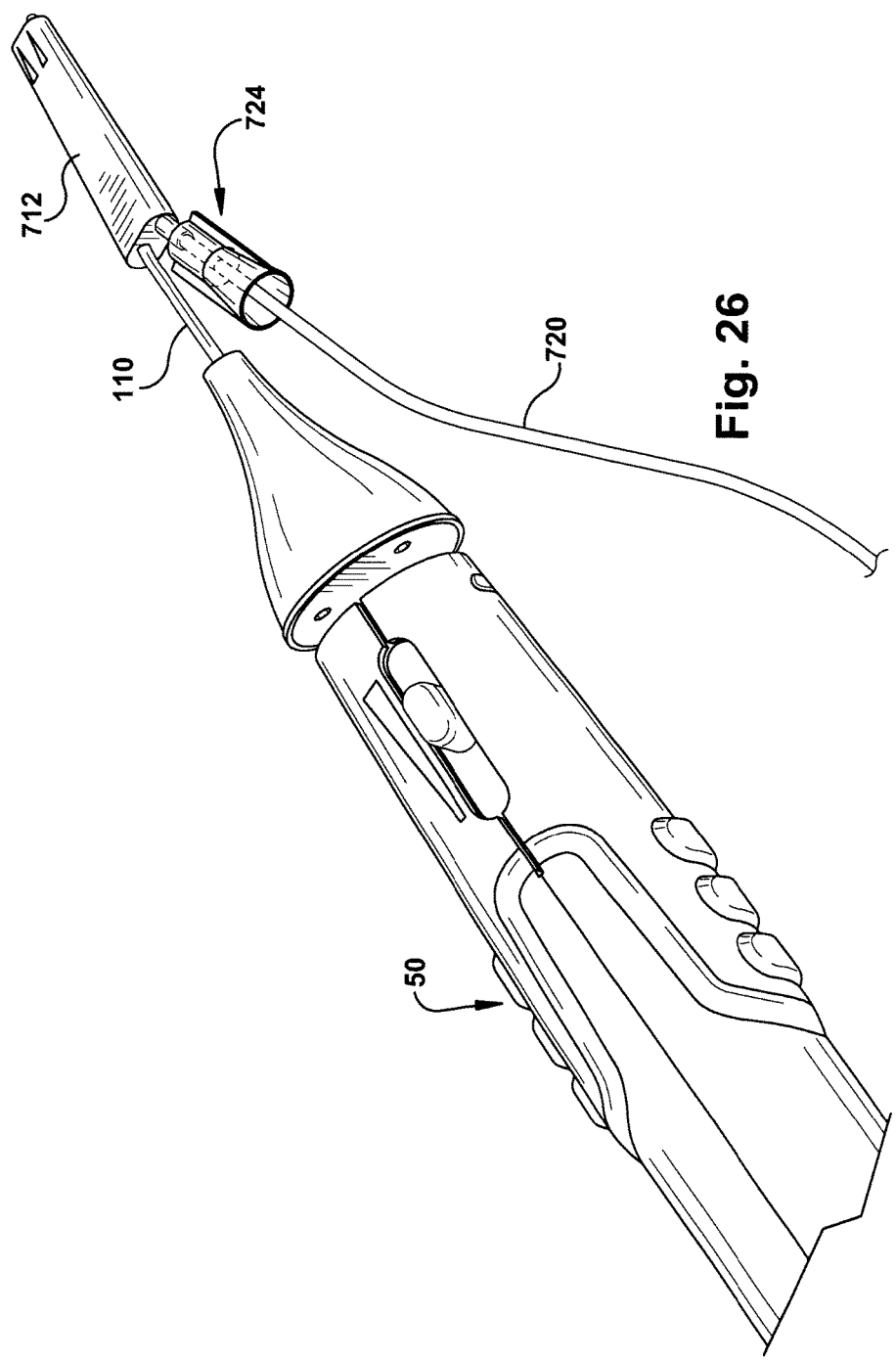
FIG. 26 is a bipolar adapter connector connected to a stimulation device.

In an embodiment illustrated in FIG. 26, the connector 712 may be configured to directly receive an electrical connection from a return operative element. For example, the connector 712 may include a plug 724 adjacent to the opening 714 to receive the operative element 110. The plug 724 may receive a luer connector or any other appropriate electrical connection. The plug 724 may be in electrical connection with the return element 716.

Figure 27:
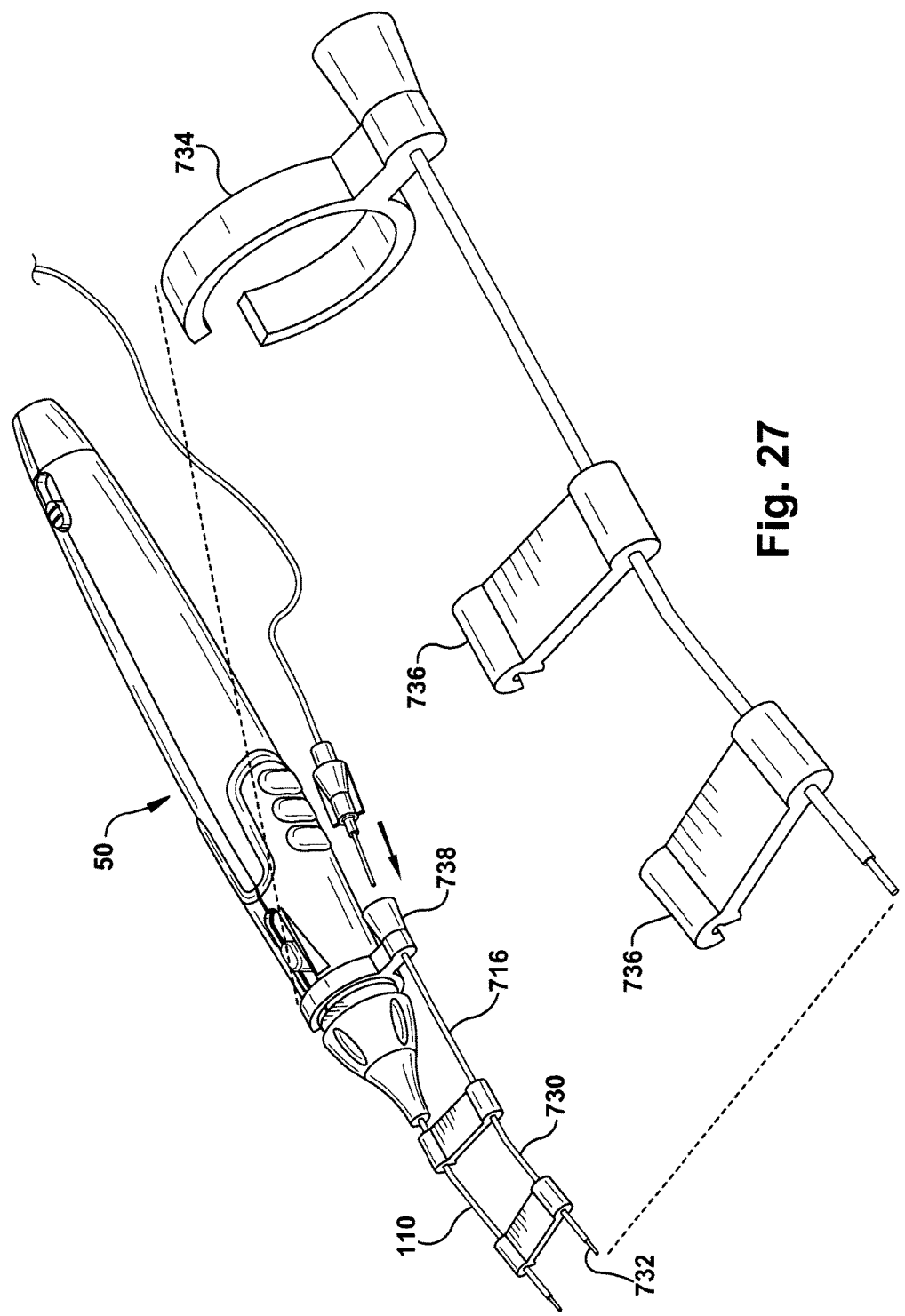
FIG. 27 is a bipolar adapter connected to a stimulation device with clips.

In an embodiment, the bipolar adapter 710 may be arranged to clip or snap onto the stimulation probe 50. The adapter 710 may include a return element 716 having an insulated portion 730 and an exposed portion 732. The adapter 710 may further include one or more clips to connect the return element 716 to the stimulation probe 50. For example, as illustrated in FIG. 27, the adapter 710 may include a first clip 734 arranged to connect to the body or housing of the stimulation probe 50. Additional clips 736 may be arranged to connect to the operative element 110 of the stimulation probe 50. The additional clips 736 may allow the return element 716 to follow the path of the operative element 110 to prevent any obstruction of users sight lines. The adapter 710 may include a receptacle 738 connected to the return element 716. The receptacle 738 may be configured to receive an electrical connector, such as a luer connection, to provide a ground or other electrical signal on the return element 716.

Figure 28:
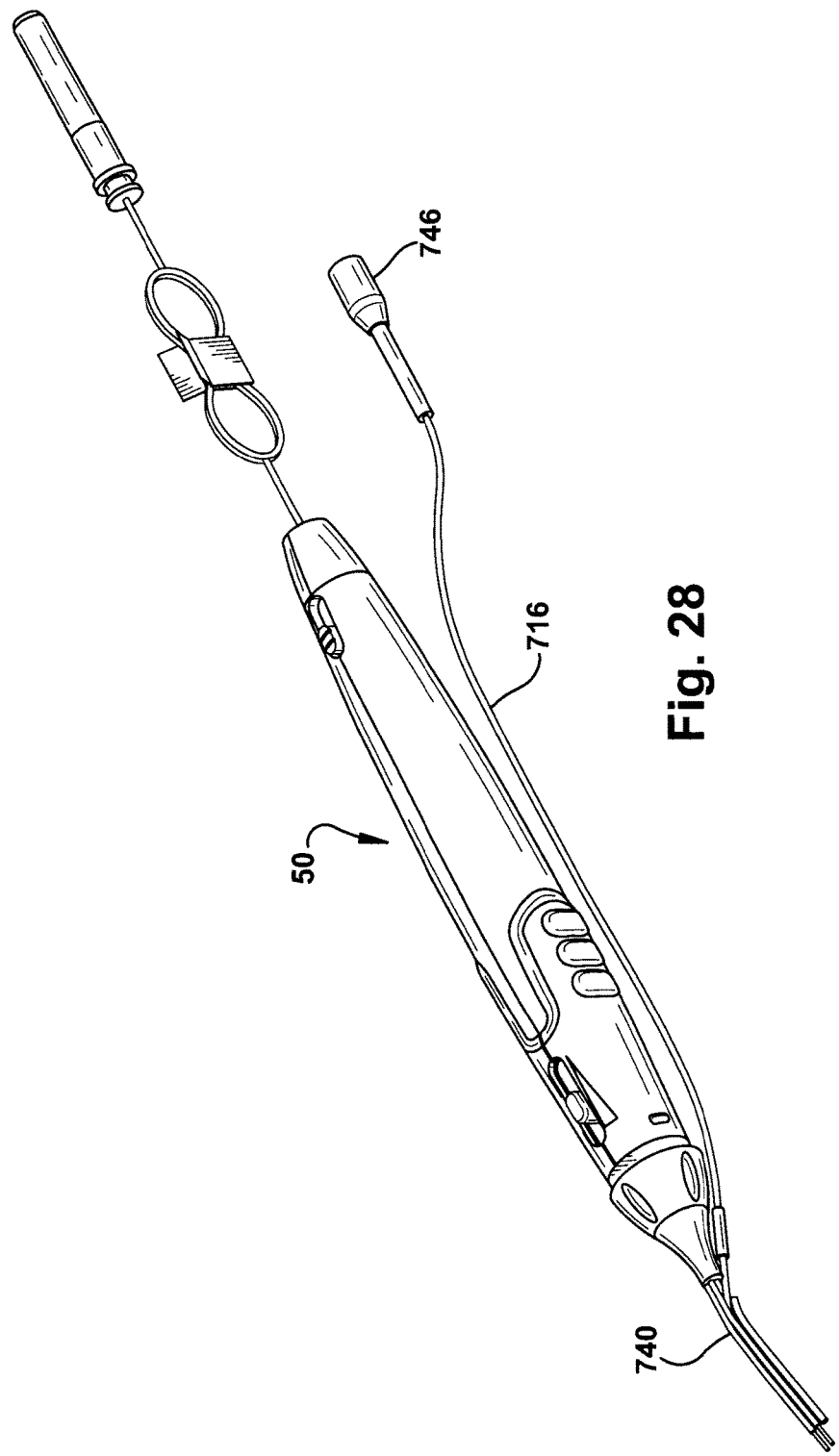
FIG. 28 is a bipolar adapter having a unitary clip.

In an embodiment, the adapter 710 may include a single unitary clip 740, as shown in FIGS. 28 and 29. The unitary clip 740 may be designed to receive both the return element 716 of the adapter and the operative element 110 of the stimulation probe 50.

The unitary clip 740 may include a first channel 742 and a second channel 744. The first channel 742 may be configured to receive the primary operative element 110 therein, and the second channel 744 may be configured to receive the return element 716 therein. The channels may be generally rounded or having a generally circular or semi-circular cross-section, or any appropriate shape to hold and retain the elements 110, 716. The channels may have different diameters to accommodate different diameters of the electrodes 110, 716. For example, the first channel 742 may be configured to receive an element having a diameter of approximately 0.04 inches while the second channel may be configured to receive an element having a diameter of approximately 0.02 inches. The channels 742, 744 may be different lengths, as shown in FIGS. 28 and 29. For example, the first channel 742 may be longer and extend to the base of the operative element 110, while the second channel 744 may be shorter and may allow the return element 716 to extend away from the body of the stimulation probe 50.

The operative element 110 may be positioned in the first channel 742 such that a tip 111 of the operative element 110 extends beyond an end of the unitary clip 740. Likewise, the return operative element 716 may be positioned in the second channel 744 such that the tip 718 of the return operative element 716 extends beyond an end of the unitary clip 740.

The unitary clip 740 may be bent or angled. For example, as shown in FIGS. 28 and 29, the unitary clip may include a first portion 750 and a bent portion 752 angled away from the first portion. The angle of the bent portion 752 may be designed to follow and match an angle of the operative element 110. The bent portion 752 may be angled downward with respect to a user holding the stimulation probe 50 to prevent any visual obstructions and allow the user to maintain a clear line of sight.

The adapter 710 may include a receptacle 746 connected to the return operative element 716. The receptacle 746 may be configured to receive an electrical connection therein, such as a needle or luer connector. The receptacle 746 may allow the return operative element 716 to be connected to electrical ground or to complete the electrical circuit of the stimulation probe 50.

The clip described in any of the above embodiments may be adjustable. For example, the clip may be malleable, slideable, or otherwise moveable to allow the distance between the operative element tip 111 and the return element tip 718 to be selectively adjusted. The user may adjust the clip to achieve the desired distance for a given application.

In an embodiment, the adapter may be a percutaneous adapter 810, as shown in FIG. 30. The percutaneous adapter 810 may be configured to allow a stimulation probe 50 to deliver a stimulation signal below the skin of a subject patient.

The percutaneous adapter 810 may include a connector 812. The connector 812 may be configured to connect to the operative element 110 of a stimulation probe 50. For example, the connector may include an opening 814 to receive the operative element 110 therein. The opening 814 may be tapered to maintain the operative element 110 in a compression fit within the connector 812. The connector may further include other retaining features, such as a set screw or clasp, to retain the connection between the connector 812 and the operative element 110.

The percutaneous adapter 810 may include a lead wire 816 extending from the connector 812. The lead wire 816 may be an electrical conductor in electrical connection with an operative element 110 inserted into the connector 812. The lead wire 816 may be any appropriate length, such as 24 inches or an length between 12 inches and 48 inches. The lead wire may further be any appropriate gauge, such as 24 AWG wire.

The percutaneous adapter 810 may include a needle 820 connected to the lead wire 816. The needle may be made of any appropriate material, such as stainless steel. Preferable, the needle may be made of an electrically conductive material and be in electrical communication with the lead wire 816. The hub 822 may be positioned at the base of the needle 820 to secure the connection between the lead wire 816 and the needle 820. A portion of the needle 820 may be insulated. For example, the needle may be insulated up to 5 millimeters away from its tip 824. The exposed tip 824 of the needle 820 may deliver an electrical stimulation signal to target tissue below the surface of the skin.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

The invention claimed is:

1. A percutaneous stimulation adapter comprising:
   a connector comprising an opening that operatively receives an electrically conductive surface of a generally rigid operative element of a stimulation control device adapted to provide stimulus current to an intended tissue to connect the connector with the operative element;
   a lead wire connected to said connector;
   a needle connected to said lead wire; and
   wherein said needle is configured to deliver a electrical stimulation signal to a target tissue located beneath the skin of a subject patient.

2. The percutaneous stimulation adapter of claim 1, wherein said connector is configured to receive and hold said operative element in position by a compression fit.

3. The percutaneous stimulation adapter of claim 1, wherein said needle is insulated up to 5 millimeters away from a tip of said needle.

4. The percutaneous stimulation adapter of claim 1, wherein said lead wire is between 12 and 48 inches long.

5. The percutaneous stimulation adapter of claim 1, wherein said needle operatively receives the electrical stimulation signal through an electrical connection to the operative element of said stimulation control device.

6. The percutaneous stimulation adapter of claim 1, wherein said opening is tapered.

7. The percutaneous stimulation adapter of claim 1, further comprising a hub disposed at a base of said needle.

8. The percutaneous stimulation adapter of claim 7, wherein said hub comprises an ergonomic gripping portion.

9. The percutaneous stimulation adapter of claim 7, wherein said hub comprises a connection between said lead wire and said base of said needle.

10. The percutaneous stimulation adapter of claim 1 wherein said needle comprises at least one of a sharp or blunt end.

11. A stimulation system comprising:
    a handheld stimulation control device comprising:
      a housing; and
      an operative element extending outward from said housing, said operative element being generally rigid and providing stimulus current to an intended tissue;
    a percutaneous stimulation adapter comprising:
      a connector operatively connected to said operative element of said stimulation control device, said connector comprising an opening to receive said operative element;
      a lead wire connected to said connector; and
      a needle electrically connected to said lead wire,
    wherein said stimulation control device operatively controls an electrical stimulation signal transmitted through said needle.

12. The stimulation system of claim 11, wherein said connector is configured to compression fit with said operative element.

13. The stimulation system of claim 11, wherein said connector comprises at least one of a screw or clasp.

14. The stimulation system of claim 11, wherein said operative element comprises a probe.

15. The stimulation system of claim 11, further comprising a hub disposed at a base of said needle, wherein said hub comprises a gripping portion.

16. The stimulation system of claim 11, wherein said needle comprises a bend such that a first part of said needle is at an angle from a second part of said needle.

17. A stimulation adapter comprising:
    a connector attachable proximal an electrically exposed portion of a generally rigid operative element of a handheld stimulation control device, wherein said connector comprises an electrically conductive member and an opening to receive said operative element and wherein said operative element provides a stimulus current to an intended tissue;
    a lead wire extending from said connector and in electrical communication with said conductive member;
    a needle in electrical communication with said lead wire; and
    wherein said needle is configured to deliver a electrical stimulation signal to a target region of a subject patient.

18. The stimulation adapter of claim 17, further comprising a hub, wherein said needle protrudes from said hub, and wherein said hub comprises gripping portion.

19. The stimulation adapter of claim 17, wherein said needle comprises an electrode.

20. The stimulation adapter of claim 17, wherein said needle comprises a blunt probe.

21. The stimulation adapter of claim 17, where said needle comprises a pliable material.

* * * * *